(12) United States Patent
Matsuda et al.

(10) Patent No.: US 9,804,174 B2
(45) Date of Patent: Oct. 31, 2017

(54) BIOMARKER FOR PARKINSON'S DISEASE AND USE THEREOF

(71) Applicant: TOKYO METROPOLITAN INSTITUTE OF MEDICAL SCIENCE, Tokyo (JP)

(72) Inventors: Noriyuki Matsuda, Tokyo (JP); Fumika Koyano, Tokyo (JP); Kei Okatsu, Tokyo (JP); Etsu Go, Tokyo (JP); Mayumi Kimura, Tokyo (JP); Yasushi Saeki, Tokyo (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 0 days.

(21) Appl. No.: 15/119,645

(22) PCT Filed: Feb. 13, 2015

(86) PCT No.: PCT/JP2015/053930
§ 371 (c)(1),
(2) Date: Aug. 17, 2016

(87) PCT Pub. No.: WO2015/125702
PCT Pub. Date: Aug. 27, 2015

(65) Prior Publication Data
US 2017/0010285 A1 Jan. 12, 2017

(30) Foreign Application Priority Data
Feb. 18, 2014 (JP) .................................. 2014-028449

(51) Int. Cl.
| | |
|---|---|
| *C07K 16/18* | (2006.01) |
| *G01N 33/68* | (2006.01) |
| *C07K 14/47* | (2006.01) |
| *C12Q 1/48* | (2006.01) |
| *G01N 33/50* | (2006.01) |
| *A61K 38/00* | (2006.01) |

(52) U.S. Cl.
CPC ......... *G01N 33/6896* (2013.01); *C07K 14/47* (2013.01); *C07K 16/18* (2013.01); *C12Q 1/485* (2013.01); *C12Y 207/11001* (2013.01); *G01N 33/5079* (2013.01); *A61K 38/00* (2013.01); *G01N 2333/47* (2013.01); *G01N 2333/912* (2013.01); *G01N 2333/91215* (2013.01); *G01N 2440/14* (2013.01); *G01N 2500/00* (2013.01); *G01N 2500/20* (2013.01); *G01N 2800/2835* (2013.01)

(58) Field of Classification Search
None
See application file for complete search history.

(56) References Cited

FOREIGN PATENT DOCUMENTS

| | | |
|---|---|---|
| JP | 201425764 A | 2/2014 |
| WO | WO 2010/005077 A1 | 1/2010 |
| WO | WO 2013/153386 A1 | 10/2013 |

OTHER PUBLICATIONS

Ardelt et al., PLoS One, 10(3):e0118646, 2015.*
Clark et al. "Drosophila pink1 is required for mitochondrial function and interacts genetically with parkin", *Nature* 441:1162-1166 (2006).
Iguchi et al. "Parkin-catalyzed Ubiquitin-Ester Transfer is Triggered by PINK1-dependent Phosphorylation", *Journal of Biological Chemistry* 288(30):22019-22032 (2013).
Kanao, "The molecular mechanism underlying PINK1-madiated mitochondrial maintenance", *Grants-in-Aid Scientific Research* (Kagaku Kenkyuhi Hojokin) Kenkyu Seika Hokokusho, Aug. 27, 2013 (Aug. 27, 2013) 4 pages.
Kane et al. "PINK1 phosphorylates ubiquitin to activate Parkin E3 ubiquitin ligase activity", *J. Cell Biol.* 205(2):143-153 (2014).
Kazlauskaite et al. "Parkin is activated by PINK1-dependent phosphorylation of ubiquitin at Ser$^{85}$ ", *Biochem. J.* 460:127-139 (2014).
Kazlauskaite et al. "PINK1 and Parkin—mitochondrial interplay between phosphorylation and ubiquitylation in Parkinson's disease", *FEBS Journal* 282:215-223 (2015).
Kitada et al. "Mutations in the parkin gene cause autosomal recessive juvenile parkinsonism", *Nature* 392:605-608 (1998).
Koyano et al. "Ubiquitin is phosphorylated by PINK1 to activate parkin", *Nature* 510:162-166 (2014).
Matsuda et al. "PINK1 stabilized by mitochondrial depolarization recruits Parkin to damaged mitochondria and activates latent Parkin for mitophagy", *J. Cell Biol.* 189(2):211-221 (2010).
Matsuda "The molecular basis for how E3 activity of Parkin IS re-established by damaged mitochondria", *Journal of Clinical and Experimental Medicine* 247(10):1013-1018 (2013).
Matsuda "Idensei Parkinson-byo Kanren Bunshi PINKI nl yotte Rinsan-ka sareta Ubiquitin ga Parkin 0 Kasseika suru", *Cell technology* 33(9):974-976 (2014).
Shiba-Fukushima et al. "PINK1-mediated phosphorylation of the Parkin ubiquitin-like domain primes mitochondrial translocation of Parkin and regulates mitophagy", *Science Reports* 2:1-8 (2012).
International Search Report corresponding to International Application No. PCT/JP2015/053930 dated Apr. 28, 2015.
Extended European Search Report corresponding to related European Patent Application No. 15751770.7 (10 pages) (dated Jul. 31, 2017).
Kondapalli et al. "PINK1 is activated by mitochondrial membrane potential depolarization and stimulates Parkin E3 ligase activity by phosphorylating Serine 65" *Open Biology* 2:1-17 (2012).

* cited by examiner

*Primary Examiner* — Kimberly A. Ballard
*Assistant Examiner* — Stacey MacFarlane
(74) *Attorney, Agent, or Firm* — Myers Bigel, P.A.

(57) ABSTRACT

A antibody has as a target molecule a ubiquitin protein comprising a phosphorylated serine residue at position 65. In addition, a method is provided for specifically detecting Parkinson's disease at an early stage, in which a target molecule is a ubiquitin protein comprising a phosphorylated serine residue at position 65, a pharmaceutical composition for definitively treating or preventing Parkinson's disease, and a method for screening for the pharmaceutical composition.

2 Claims, 12 Drawing Sheets

BIOMARKER FOR PARKINSON'S DISEASE AND USE THEREOF

RELATED APPLICATIONS

This application is a 35 U.S.C. §371 national phase application of PCT Application PCT/JP2015/053930 filed Feb. 13, 2015, which claims priority to Japanese Application No. 2014-028449 filed Feb. 18, 2014. The entire content of each are incorporated herein by reference in its entirety.

STATEMENT REGARDING ELECTRONIC FILING OF A SEQUENCE LISTING

A Sequence Listing in ASCII text format, submitted under 37 C.F.R. §1.821, entitled 5576-325_ST25.txt, 1,956 bytes in size, generated on Aug. 15, 2016, and filed via EFS-Web, is provided in lieu of a paper copy. This Sequence Listing is hereby incorporated by reference into the specification for its disclosures.

The present invention relates to a biomarker for the diagnosis of Parkinson's disease, an antibody against the same, a method for testing for and/or diagnosing Parkinson's disease, and a therapeutic agent or a preventive agent for Parkinson's disease and a screening method therefor.

FIELD AND BACKGROUND OF THE INVENTION

Parkinson's disease is a neurodegenerative disease which develops with high frequency with aging, and the incidence rate is more than 1% of the population aged 65 and over. It is anticipated that the number of patients with Parkinson's disease will significantly increase in association with the aging of the population in the future, and thus, it is imperative to promptly establish methods for diagnosing, preventing and/or treating Parkinson's disease.

It has been known that Parkinson's disease is developed by degeneration and/or defluxion of dopamine neurons in the substantia nigra in the midbrain. A dopamine replacement therapy involving administration of L-dopa has been carried out as the primary prognosis treatment for Parkinson's disease. However, the dopamine replacement therapy merely treats symptoms, and thus, in order to suppress the symptoms of Parkinson's disease, drug administration must be continued. Moreover, the dopamine replacement therapy has been problematic in that long-term administration of L-dopa produces progressively less effect caused by shortened duration of medicinal effects or serious side effects such as abnormal involuntary movement called "dyskinesia". In addition, for diagnosis of Parkinson's disease, there is only a diagnostic method based on symptoms characteristic of this disease. Thus, under the current circumstances, Parkinson's disease cannot be clearly distinguished from other neurological diseases at an early stage with mild symptoms. In order to establish a radical therapy for Parkinson's disease and a method for specifically diagnosing this disease at an early stage, it is necessary to elucidate the mechanism of pathogenesis of Parkinson's disease, that is, the mechanism by which degeneration of dopamine neurons progresses. It has been desired to promptly elucidate such mechanisms.

The majority of cases of Parkinson's disease develop sporadically, but some cases are familial (hereditary) diseases. Multiple associated genes have been isolated and identified. Since sporadic Parkinson's disease shares clinical symptoms with familial Parkinson's disease, it has been assumed that the two typos of Parkinson's diseases would have a common mechanism of degeneration of dopamine cells, and thus, it has been anticipated that analysis of genes responsible for hereditary Parkinson's disease would lead to elucidation of the pathogenic mechanism of sporadic Parkinson's disease. PINK1 and Parkin have been identified as causal genes responsible for hereditary recessive early-onset Parkinsonism (Non Patent Document 1). PINK1 encodes Ser/Thr kinase localized in mitochondria, and Parkin encodes ubiquitin ligase (E3). When mitochondria lose their membrane potential, PINK1 and Parkin accumulate on mitochondria and they ubiquitinate the mitochondria, so as to induce only defective mitochondria to selective degradation (Non-Patent Document 2). An abnormality in this selective degradation mechanism of defective mitochondria (mitophagy) is considered to be a cause of neurodegeneration in Parkinson's disease.

Parkin is ubiquitin ligase (E3). E3 is the most important enzyme for determining substrate specificity in a ubiquitin-proteasome system, and in order to elucidate the pathogenic mechanism of Parkinson's disease due to abnormal mitophagy, it is extremely important to understand the mechanism of activation of Parkin. Parkin is generally present in the cytoplasm in an inactive form. When Parkin is recruited to defective mitochondria, it is activated and functions as an E3 enzyme. It has been known that PINK1 is essential for both recruitment of Parkin to mitochondria and the activation thereof (Non-Patent Document 3). Moreover, as a result of recent studies, it has been found that the autophosphorylation of PINK1 occurs with a reduction in the mitochondrial membrane potential, and thereby Parkin is phosphorylated in a PINK1-dependent manner, and as a result, Parkin is recruited to the mitochondria and is activated as an E3 enzyme (Non-Patent Document 4 and Non-Patent Document 5). However, it also has been confirmed that phosphorylation of Parkin is essential, but not sufficient, for the activation thereof. Hence, the mechanism of activation of Parkin is still only partially understood.

Parkin, which has been activated as an E3 enzyme, ubiquitinates a substrate protein on the mitochondrial outer membrane to induce the mitochondria to degrade. Ubiquitin is a protein consisting of 76 amino acids, which universally exists in all eukaryotes, and the amino acid sequence thereof is highly conserved. Studies regarding such ubiquitin have a long history, and it has been revealed that the ubiquitin acts as a tag for inducing the degradation of a substrate protein, and at the same time, it is involved in various functions such as DNA repair or intracellular signaling. Moreover, it has been studied in detail that the ubiquitin has seven lysine residues, and that the ubiquitin binds to a glycine residue at the C-terminus of another ubiquitin via these lysine residues to form a polyubiquitin chain, and various different functions are exhibited depending on the binding pattern (i.e., a difference in the shape of a polyubiquitin chain). However, it has not thus far been reported that the ubiquitin itself has undergone a certain posttranslational modification, and as a result, its function is changed.

CITATION LIST

Non-Patent Document

Non-Patent Document 1: Nature, Vol. 392, pp. 605-608 (1998)
Non-Patent Document 2: Nature, Vol. 441, pp. 1162-1166 (2006)

Non-Patent Document 3: J. Cell Biol., Vol. 189, pp. 211-221 (2010)

Non-Patent Document 4: Sci. Rep., Vol. 2, srep 01002 (2012)

Non-Patent Document 5: J. Biol. Chem., Vol. 288, pp. 22019-22012 (2013)

SUMMARY OF INVENTION

Technical Problem

It is an object of the present invention to elucidate the mechanism of activation of Parkin, and to provide early diagnosis, prevention and definitive treatment of Parkinson's disease, based on the elucidated mechanism.

Solution to Problem

As a result of intensive research, the present inventors have found that phosphorylation of ubiquitin, as well as phosphorylation of Parkin, is essential for complete activation of the Parkin. The finding that phosphorylation of ubiquitin is essential for activation of Parkin is novel. Moreover, the findings that the ubiquitin itself undergoes a certain posttranslational modification, and that the ubiquitin is thereby involved in the control of intracellular signaling, are previously completely unknown, and these are surprising discoveries. Based on these novel discoveries, the present inventors have found that a phosphorylated ubiquitin is useful for the detection, diagnosis, prevention and treatment of Parkinson's disease, and also for screening for a preventive and/or a therapeutic agent of Parkinson's disease.

Specifically, according to one embodiment, the present invention provides a method for testing for Parkinson's disease, which comprises a step of detecting or quantifying a ubiquitin protein comprising a phosphorylated serine residue at position 65 in a sample isolated from a subject.

The step of detecting or quantifying is preferably carried out by an immunological technique.

In addition, according to one embodiment, the present invention provides a biomarker for detecting Parkinson's disease, which consists of a ubiquitin protein comprising a phosphorylated serine residue at position 65.

Moreover, according to one embodiment, the present invention provides an antibody having an ability to specifically bind to a ubiquitin protein comprising a phosphorylated serine residue at position 65.

The antibody is preferably a polyclonal antibody or a monoclonal antibody.

Furthermore, according to one embodiment, the present invention provides a therapeutic agent or a preventive agent for Parkinson's disease, which comprises a ubiquitin protein comprising a phosphorylated serine residue at position 65.

Further, according to one embodiment, the present invention provides a therapeutic agent or a preventive agent for Parkinson's disease, which comprises a phosphorylation-mimicking form of ubiquitin, in which the serine residue at position 65 is substituted with an aspartic acid residue.

Still further, according to one embodiment, the present invention provides a method for screening, for a therapeutic agent or a preventive agent for Parkinson's disease, which comprises: (1) a step of providing cells that express PINK1; (2) a step of damaging mitochondria in the cells; (3) a step of contacting the cells with a candidate compound; and (4) a step of measuring the amount of a ubiquitin protein comprising a phosphorylated serine residue at position 65, which has been generated in the cells.

Still further, according, to one embodiment, the present invention provides a method for screening for a therapeutic agent or a preventive agent for Parkinson's disease, which comprises: (1) a step of preparing a phosphorylation reaction solution containing a ubiquitin protein, a kinase, and a phosphate donor; (2) a step of adding a candidate compound to the phosphorylation reaction solution; and (3) a step of measuring the amount of a ubiquitin protein comprising a phosphorylated serine residue at position 65, which has been generated in the phosphorylation reaction solution.

The phosphorylation reaction solution is preferably a cell extract.

Advantageous Effects of Invention

The phosphorylated ubiquitin according to the present invention is useful as a biomarker capable of measuring and/or evaluating the pathogenic process of Parkinson's disease, for an early and specific diagnosis of Parkinson's disease, or for the screening of a therapeutic agent or a preventive agent for Parkinson's disease. In addition, the antibody according to the present invention having an ability to specifically bind to the phosphorylated ubiquitin is useful for the detection and/or measurement of the biomarker.

Moreover, the phosphorylated ubiquitin and phosphorylation-mimicking form of ubiquitin according to the present invention are useful as therapeutic agents or preventive agents for Parkinson's disease, and these substances enable an early and definitive treatment of Parkinson's disease.

DESCRIPTION OF EMBODIMENTS

Figure 1:
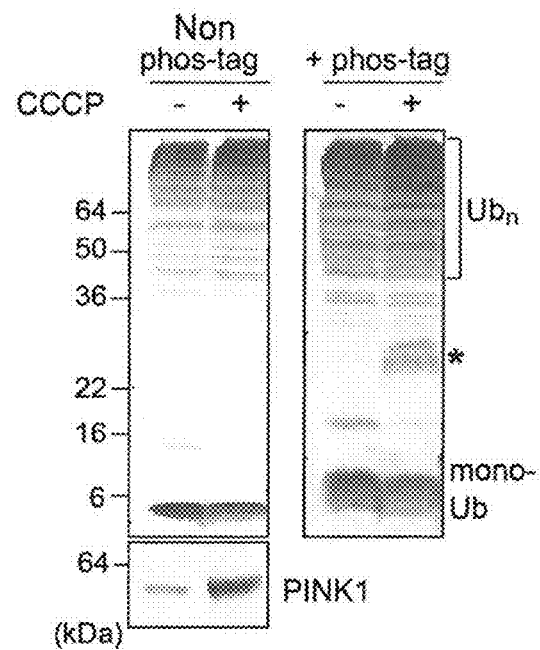
FIG. 1 is a view, in which the phosphorylation of ubiquitin in CCCP-treated cells has been confirmed by a Phos-tag assay.

Hereinafter, the present invention will be described in detail. However, the present invention is not limited to embodiments described in the present description.

A first aspect of the present invention relates to early detection of Parkinson's disease. In this aspect, a biomarker for detecting Parkinson's disease and an intended use thereof are provided.

According to one embodiment, the present invention is a biomarker for detecting Parkinson's disease, which consists of a ubiquitin protein comprising a phosphorylated serine residue at position 65. The "biomarker for detecting Parkinson's disease" of the present embodiment means a biomolecule serving as an indicator for detecting the presence or absence of affection with Parkinson's disease or the degree of the affection.

The "Parkinson's disease" is a neurodegenerative disease, which clinically has at least two symptoms selected from among (1) muscular rigidity of limbs, (2) involuntary movements such as resting tremor, (3) hypokinesia or akinesia, and (4) postural reflex impairment, and which is pathologically characterized by degeneration and defluxion of dopamine neurons in the substantia nigra. The "Parkinson's disease" according to the present invention includes early-onset Parkinsonism, familial (hereditary) Parkinsonism, striatonigral degeneration (multiple system atrophy), and the like, as well as what is called Parkinson's disease (sporadic Parkinson's disease).

The biomarker for detecting Parkinson's disease of the present embodiment consists of a ubiquitin protein comprising a phosphorylated serine residue at position 65. Hereinafter, in the present description, a ubiquitin protein comprising a phosphorylated serine residue at position 65 is referred to as "Ser65-phosphorylated ubiquitin".

The "Ser65-phosphorylated ubiquitin" of the present embodiment may include not only a ubiquitin protein consisting of a specific amino acid sequence (SEQ ID NO: 1), but also a ubiquitin protein consisting of an amino acid sequence comprising a substitution, deletion, insertion and/or addition of one to several amino acids with respect to the amino acid sequence shown in SEQ ID NO: 1, on condition that the phosphorylated serine residue at position 65 is conserved. Herein, "one to several" is preferably "1 to 3," "1 or 2," or "1".

Moreover, the "Ser65-phosphorylated ubiquitin" of the present embodiment may include a ubiquitin protein consisting of an amino acid sequence having an identity of 80% or more with SEQ ID NO: 1, on condition that the phosphorylated serine residue at position 65 is conserved and physiological functions equivalent to those of the ubiquitin consisting of SEQ ID NO: 1 are maintained. The amino acid sequence identity is preferably approximately 90% or more, 95% or more, 96% or more, or 97% or more, and particularly preferably 98% or more, or 99% or more. The amino acid sequence identity can be determined using sequence analysis software, or using program commonly used in the present technical field (FASTA, BLAST, etc.).

The biomarker for detecting Parkinson's disease of the present embodiment is generated as a result of mitochondria abnormality occurring, and it then disappears in a normal subject (not affected with Parkinson's disease). However, in a Parkinson's disease patient, it is anticipated that the biomarker will not be generated due to the loss of function of PINK1, or that the concentration thereof will be increased by the loss of function of Parkin or by acceleration in mitochondrial stress. That is to say, the biomarker for detecting Parkinson's disease of the present embodiment is able to specifically detect Parkinson's disease at an early stage, by using, as an indicator, a deviation (a reduction or an increase) from the normal value of a subject who is not affected with Parkinson's disease.

According to one embodiment, the present invention is a method for testing for Parkinson's disease, which comprises a step of detecting or quantifying a biomarker for detecting Parkinson's disease consisting of a Ser65-phosphorylated ubiquitin protein in a sample isolated from a subject.

The term "test" may be used in the present embodiment to mean that Parkinson's disease is numerically quantified or the presence or absence of Parkinson's disease is detected by using a biomarker for detecting Parkinson's disease consisting of a Ser65-phosphorylated ubiquitin protein as an indicator. Based on the test results, a physician is able to determine and/or diagnose whether or not the subject is affected by Parkinson's disease, and then, is able to determine appropriate therapeutic strategies.

The term "subject" is used in the present embodiment to mean an individual animal, which can be affected with Parkinson's disease. Examples of the animal include a mouse, a rat, a rabbit, a dog, non-human primates, and mammals such as a human. The animal is preferably a human.

The "sample" of the present embodiment is a biological sample, which can be collected from a subject. The sample may be, for example, tissues, cells, body fluid and the like, which are derived from a subject, but the examples are not particularly limited thereto. Examples of the tissue sample or the cell sample may include brain, cardiac muscle, and skeletal muscle. Examples of the body fluid may include blood, plasma, serum, and cerebrospinal fluid. Such a sample can be obtained from a subject by a method well known to a person skilled in the art.

In the present embodiment, a Ser65-phosphorylated ubiquitin protein can be detected or quantified by a method well known in the present technical field. Examples of the method for detecting or quantifying the Ser65-phosphorylated ubiquitin include immunological techniques such as enzyme immunoassay (EIA), radioimmunoassay (RIA), immunoblotting, immunoprecipitation or immunohistochemical staining, and methods such as liquid chromatography or mass spectrometry. A preferred detection or quantification method is an immunological technique. Detection or quantification of the Ser65-phosphorylated ubiquitin by an immunological technique can be carried out, for example, by using an antibody having an ability to specifically bind to the Ser65-phosphorylated ubiquitin.

When the Ser65-phosphorylated ubiquitin is detected or quantified by mass spectrometry, ubiquitin purified from a sample is cleaved by protease such as trypsin or endoproteinase Lys-C, and then, for example, a signal derived from a peptide fragment: E(pS)TLHLVLR (corresponding to the amino acids at positions 64 to 72 of phosphorylated ubiquitin), in which the m/z of a precursor ion (Precursor m/z) is 574.297 and the charge state is +2, is detected. Moreover, at that time, a signal derived from a peptide fragment: ESTLHLVLR (corresponding to the amino acids at positions 64 to 72 of non-phosphorylated ubiquitin), in which the m/z of a precursor ion is 534.314 and the charge state is +2, can be detected as a positive control.

The method for testing for Parkinson's disease of the present embodiment may further comprise a step of comparing the results of the above described detection or quantification with the predetermined biomarker profiles with regard to a sample derived from a control which is not affected with Parkinson's disease (a normal control sample). Based on the comparison results, if the biomarker for detecting Parkinson's disease in the subject-derived sample is significantly deviated from a normal value, it is determined that the subject is likely to be affected with Parkinson's disease. In this sense, the method for testing for Parkinson's disease of the present embodiment can also be a method for evaluating and determining whether or not a subject is affected with Parkinson's disease, that is, a diagnostic method. In addition, the detection or quantification results in a single person may be compared between before and after administration of a therapeutic agent, so that the therapeutic effects can be determined.

The method for testing for Parkinson's disease of the present embodiment enables early and specific detection of Parkinson's disease, and thus, it is extremely useful.

According to one embodiment, the present invention is an antibody having an ability to specifically bind to a Ser65-phosphorylated ubiquitin protein. Hereinafter, in the present description, the antibody having an ability to specifically bind to the Ser65-phosphorylated ubiquitin protein is referred to as an "anti-Ser65-phosphorylated ubiquitin antibody."

The "antibody" of the present embodiment may be a polyclonal antibody, a monoclonal antibody, a chimeric antibody, a humanized antibody, or an antibody fragment such as Fab, F(ab')$_2$ or scFv. These antibodies can be produced by methods well known in the present technical field. The antibody of the present embodiment is preferably a polyclonal antibody or a monoclonal antibody.

Specifically, when the antibody of the present embodiment is a polyclonal antibody, the Ser65-phosphorylated ubiquitin or a partial peptide thereof (a fragment comprising phosphorylated Ser 65 and having a length of 6 to 30 amino acids, and preferably 9 to 25 amino acids) may be used as an antigen, and a mammal such as a rat, a rabbit, a guinea pig or a goat is immunized with the antigen. Thereafter, serum is recovered from the animal, and is then purified, so as to obtain a polyclonal antibody.

On the other hand, when the antibody of the present embodiment is a monoclonal antibody, antibody-producing cells are recovered from an immunized animal that has been produced by the same procedures as those described above, and the antibody-producing cells are then fused with myeloma cells to prepare hybridomas. Thereafter, hybridoma clones producing an antibody exhibiting a highly specific affinity for the antigen are selected, and a culture solution of the selected clones is recovered and is then purified, so as to obtain a monoclonal antibody.

The chimeric antibody is a monoclonal antibody produced by genetic engineering. A specific example of the chimeric antibody may be an antibody, the variable region of which is derived from the immunoglobulin of an animal other than a human and the constant region of which is derived from human immunoglobulin. The animal other than a human is not particularly limited, as long as it is able to produce hybridomas, and examples of such an animal include a mouse, a rat, and a rabbit. The chimeric antibody can be produced by a method well known in the present technical field.

The humanized antibody (i.e., a CDR-grafted humanized antibody) is a monoclonal antibody produced by genetic engineering. Specifically, the humanized antibody means an antibody, in which a part or all of complementarity-determining regions in the hypervariable region thereof are derived from the monoclonal antibody of an animal other than a human, and the framework region in the variable region thereof is derived from human immunoglobulin, and the constant region thereof is derived from human immunoglobulin. The humanized antibody can be produced by a method well known in the present technical field.

The antibody fragment, such as Fab, F(ab')$_2$ or scFv, is a portion comprising the antigen-binding region of the above-described antibody, or a portion derived from the region. The antibody fragment can be produced by a method well known in the present technical field.

The anti-Ser65-phosphorylated ubiquitin antibody of the present embodiment can be used to detect or quantify a Ser65-phosphorylated ubiquitin protein in cells or tissues.

The anti-Ser65-phosphorylated ubiquitin antibody of the present embodiment can also be used as a reagent for testing for Parkinson's disease by being bound to any given labeling substance. Herein, any given labeling substance may be all labeling substances used for nucleic acid, which are known in the present technical field. Examples of the labeling substance include biotin, fluorescent dyes, luminescent substances, radioisotopes, and enzymes. Moreover, the reagent for detecting the Ser65-phosphorylated ubiquitin may be further combined with additional elements, such as a container, a buffer, a positive control, a negative control and test protocols, as necessary, so as to produce a kit for testing for Parkinson's disease.

In a second aspect, the present invention relates to the treatment or prevention of Parkinson's disease. In this aspect, a therapeutic agent or a preventive agent for Parkinson's disease is provided.

That is, according to one embodiment, the present invention is a therapeutic agent or a preventive agent for Parkinson's disease, which comprises a Ser65-phosphorylated ubiquitin protein. The Ser65-phosphorylated ubiquitin can activate Parkin and normalize mitophagy, so as to definitively treat or prevent Parkinson's disease.

In the present invention, the term "treatment" does not only include complete cure of Parkinson's disease, but it may also include remission of the symptoms of Parkinson's disease, alleviation of the conditions thereof, and retardation or halt of the progression of the pathologic conditions thereof.

The Ser65-phosphorylated ubiquitin according to the present embodiment may include not only a ubiquitin protein consisting of a specific amino acid sequence (SEQ ID NO: 1), but also a ubiquitin protein consisting of an amino acid sequence comprising a substitution, deletion, insertion and/or addition of one to several amino acids with respect to the amino acid sequence shown in SEQ ID NO: 1, on condition that the phosphorylated serine residue at position 65 is conserved. Herein, "one to several" is preferably "1 to 3," "1 or 2," or "1".

Moreover, the "Ser65-phosphorylated ubiquitin" of the present embodiment may include a ubiquitin protein consisting of an amino acid sequence having an identity of 80% or more with SEQ ID NO: 1, on condition that the phosphorylated serine residue at position 65 is conserved and physiological functions equivalent to those of the ubiquitin consisting of SEQ ID NO: 1 are maintained. The amino acid sequence identity is preferably approximately 90% or more, 95% or more, 96% or more, or 97% or more, and particularly preferably 98% or more, or 99% or more. The amino acid sequence identity can be determined using sequence analysis software, or using a program commonly used in the present technical field (PASTA, BLAST, etc.).

The Ser65-phosphorylated ubiquitin of the present embodiment can be produced by biosynthesis involving a genetic engineering method, or chemical synthesis.

When the Ser65-phosphorylated ubiquitin is produced by biosynthesis involving a genetic engineering method, host cells may be transformed, for example, with an expression vector comprising DNA encoding a ubiquitin protein, so that the ubiquitin is allowed to express in the host cells, and thereafter, the ubiquitin protein can be purified and be then phosphorylated, thereby producing a Ser65-phosphorylated ubiquitin protein.

As host cells in which a ubiquitin protein is expressed, bacteria, enzymes, mammalian cells and the like can be used, for example. Preferred examples of the host cells that can be used herein include *Escherichia coli* such as BL21 (DE3) or Rosetta (DE3), and human-derived cells such as HeLa cells, CHO cells or COS7 cells. In a case in which *Escherichia coli* are used as host cells, examples of the expression vector that can be used include *Escherichia coli* expression plasmids, such as pT7 (Sigma-Aldrich) or pET (Merck Millipore). In a case in which mammalian cells are used as host cells, examples of the expression vector that can be used include animal cell expression plasmids such as pcDNA3.1 (Invitrogen), and animal virus vectors such as retroviruses or adenoviruses. The transformation can be carried out by well-known methods such as a calcium phosphate co-precipitation method, an electroporation method, a microinjection method or a lipofection method.

Phosphorylation of ubiquitin can be carried out by allowing ubiquitin isolated and purified from host cells to react with mitochondria in which PINK is accumulated by reducing membrane potential, or with an immunoprecipitation product comprising PINK1, or with PINK1. The reaction can be carried out in a buffer containing divalent ions such as magnesium and a phosphate donor such as ATP.

When the Ser65-phosphorylated ubiquitin is produced by chemical synthesis, for example, a ubiquitin protein may be synthesized using a peptide synthesizer, and it may be then subjected to a phosphorylation modification to produce the Ser65-phosphorylated ubiquitin. Operations for carrying out such chemical synthesis can be all carried out by known methods.

The Ser65-phosphorylated ubiquitin of the present embodiment may also be fused with a cell membrane penetrating peptide at the carboxyl terminus thereof. The cell membrane penetrating peptide-fused Ser65-phosphorylated ubiquitin is preferable because it can be efficiently delivered into a cell. The cell membrane penetrating peptide may be a peptide comprising a large amount of basic amino acid such as arginine or lysine and having the property of penetrating into a cell membrane. Examples of the cell membrane penetrating peptide of the present embodiment include, but are not limited to, HIV-1 Tat, HIV-1 Rev, BMV-gag, and HTLV-IIRex.

The therapeutic agent or preventive agent for Parkinson's disease according to the present embodiment comprises a Ser65-phosphorylated ubiquitin protein, as an active ingredient. This therapeutic agent or preventive agent may be composed of only the active ingredient, but it may also comprise, as any given components, a pharmaceutically acceptable known diluent, carrier, excipient, and other components.

In order to produce the therapeutic agent or preventive agent for Parkinson's disease according to the present embodiment, the Ser65-phosphorylated ubiquitin may be combined with the above-described known diluent, carrier, excipient, and other components, as necessary, to prepare a formulation. The Ser65-phosphorylated ubiquitin may be comprised, as an active ingredient, in the therapeutic agent or preventive agent for Parkinson's disease, such that it can be an appropriate dose within a range that depends on each dosage form. The content of the Ser65-phosphorylated ubiquitin in the agent is preferably determined, such that the dose of the Ser65-phosphorylated ubiquitin per adult per day can be generally 0.001 mg/kg (body weight) or more, and preferably 0.01 mg/kg (body weight) or more. However, the content of the Ser65-phosphorylated ubiquitin is not limited to the aforementioned range, and it can be appropriately adjusted depending on symptoms, age, sex and the like of a patient. The upper limit of the dose per day is preferably 10 mg/kg (body weight) or less, and more preferably 1 mg/kg (body weight) or less.

The therapeutic agent or preventive agent for Parkinson's disease according to the present embodiment may be formulated into a tablet, a capsule, a powder agent, a granule, a syrup agent, an injection, a rectal administration agent, and the like. Accordingly, the therapeutic agent or preventive agent for Parkinson's disease according to the present embodiment can be achieved by various methods including oral, intraperitoneal, intradermal, intravenous or intramuscular administration.

Examples of the oral preparation of the therapeutic agent or preventive agent for Parkinson's disease may include solid agents such as a tablet, a capsule, a powder agent or a granule. In this case, suitable additives, for example, additives such as starch, lactose, saccharose, mannitol, carboxymethyl cellulose, corn starch or inorganic salts, and further, as desired, a binder, a disintegrator, a lubricant, a coloring agent, a flavor, and the like, may be mixed into the therapeutic agent or preventive agent for Parkinson's disease. Otherwise, the oral preparation of the therapeutic agent or preventive agent for Parkinson's disease can be, for example, a liquid such as a syrup agent. In this case, sterile water, normal saline, ethanol or the like can be used as a carrier. Moreover, an auxiliary agent such as a suspending agent, a sweetener, a flavoring agent, an antiseptic, and the like may be added to the oral preparation of the therapeutic agent or preventive agent for Parkinson's disease, as desired.

The parenteral agent of the therapeutic agent or preventive agent for Parkinson's disease can be, for example, a liquid agent such as an injection or a rectal administration agent. In this case, the Ser65-phosphorylated ubiquitin used as an active ingredient may be dissolved or suspended in distilled water for injection, normal saline, glucose aqueous solution, vegetable oil for injection, propylene glycol, polyethylene glycol or the like according to a common method, and thereafter, a disinfectant, a stabilizer, a tonicity agent, a soothing agent and the like may be further added to the solution or suspension, as necessary, so as to prepare a parenteral agent. Otherwise, such a parenteral agent can also be prepared by producing a solid composition, and then dissolving the solid composition in sterile water or a sterile injection solvent before use.

The therapeutic agent or preventive agent for Parkinson's disease according to the present embodiment is useful for the definitive treatment or prevention of Parkinson's disease.

In addition, according to one embodiment, the present invention is a therapeutic agent or a preventive agent for Parkinson's disease, which comprises a phosphorylation-mimicking form of ubiquitin, in which the serine residue at position 65 is substituted with an aspartic acid residue. The phosphorylation-mimicking form of ubiquitin, in which the serine residue at position 65 is substituted with an aspartic acid residue, can activate Parkin and normalize mitophagy, as with the Ser65-phosphorylated ubiquitin, so as to definitively treat or prevent Parkinson's disease. Hereinafter, in the present description, the phosphorylation-mimicking form of ubiquitin, in which the serine residue at position 65 is substituted with an aspartic acid residue, is referred to as "Ser65Asp phosphorylation-mimicking ubiquitin".

The Ser65Asp phosphorylation-mimicking ubiquitin of the present embodiment may include not only a ubiquitin protein consisting of a specific amino acid sequence (SEQ ID NO: 2), but also a ubiquitin protein consisting of an amino acid sequence comprising a substitution, deletion, insertion and/or addition of one to several amino acids with respect to the amino acid sequence shown in SEQ ID NO: 2, on condition that the aspartic acid residue at position 65 is conserved. Herein, "one to several" is preferably "1 to 3," "1 or 2," or "1".

Moreover, the "Ser65Asp phosphorylation-mimicking ubiquitin" of the present embodiment may include a ubiquitin protein consisting of an amino acid sequence having an identity of 80% or more with SEQ ID NO: 2, on condition that the aspartic acid residue at position 65 is conserved and physiological functions equivalent to those of the Ser65-phosphorylated ubiquitin are maintained. The amino acid sequence identity is preferably approximately 90% or more, 95% or more, 96% or more, or 97% or more, and particularly preferably 98% or more, or 99% or more. The amino acid sequence identity can be determined using sequence analysis software, or using a program commonly used in the present technical field (FASTA, BLAST, etc.).

The Ser65Asp phosphorylation-mimicking ubiquitin of the present embodiment can be produced by biosynthesis involving a genetic engineering method, or chemical synthesis, as in the case of the above described Ser65-phosphorylated ubiquitin.

The Ser65Asp phosphorylation-mimicking ubiquitin of the present embodiment may also be fused with a cell membrane penetrating peptide at the carboxyl terminus thereof, as in the case of the above described Ser65-phosphorylated ubiquitin.

The therapeutic agent or preventive agent for Parkinson's disease according to the present embodiment comprises a Ser65Asp phosphorylation-mimicking ubiquitin protein, as an active ingredient. This therapeutic agent or preventive agent may be composed of only the active ingredient, but it may also comprise, as any given components, a pharmaceutically acceptable known diluent, carrier, excipient, and other components.

The therapeutic agent or preventive agent for Parkinson's disease according to the present embodiment can be formulated, as in the case of the above described therapeutic agent or preventive agent for Parkinson's disease comprising a Ser65-phosphorylated ubiquitin protein.

The therapeutic agent or preventive agent for Parkinson's disease according to the present embodiment is useful for the definitive treatment or prevention of Parkinson's disease.

In a third aspect, the present invention relates to the development of a novel therapeutic agent or a novel preventive agent for Parkinson's disease. In this aspect, a method for screening for a therapeutic agent or a preventive agent for Parkinson's disease is provided.

According to one embodiment, the present invention is a method for screening for a therapeutic agent or a preventive agent for Parkinson's disease, which comprises: (1) a step of providing cells that express PINK1; (2) a step of damaging mitochondria in the cells; (3) a step of contacting the cells with a candidate compound; and (4) a step of measuring the amount of a ubiquitin protein comprising a phosphorylated serine residue at position 65, which has been generated in the cells. According to the method of the present embodiment, a compound that promotes phosphorylation of the Ser 65 of a ubiquitin protein can be obtained as a substance effective for a therapeutic agent or a preventive agent for Parkinson's disease.

In the screening method of the present embodiment, cells that express PINK1 are prepared and are then used. Hereinafter, in the present description, living cells that express PINK1 are referred to as "PINK1-expressing cells".

The PINK1-expressing cells of the present embodiment can be cells collected from an individual animal. Such individual animal-derived cells can be collected from tissues expressing PINK1, for example, from the tissues of brain or muscle, according to a method well known to one skilled in the art. Examples of the individual animal include a mouse, a rat, a rabbit, a dog, non-human primates, and a human. The animal is preferably a human.

The PINK1-expressing cells of the present embodiment may be a mammalian cell line that expresses PINK1. Examples of the mammalian cell line that is preferably used herein include human-derived cell lines such as HeLa cells, CHO cells or COS7 cells.

Subsequently, mitochondria in the PINK1-expressing cells are damaged. Mitochondria can be damaged by a conventionally known method, and examples of the method include a CCCP treatment, a rotenone treatment, a paraquat treatment, and an MPTP treatment.

Subsequently, a candidate compound is contacted with PINK1-expressing cells, in which mitochondria are damaged. Examples of the candidate compound may be a protein, a peptide, a nucleic acid, a non-peptide compound, a synthetic compound, a cell extract, a plant extract, and an animal tissue extract. These substances may be either novel substances or known substances.

The above-described contact of the cells with a candidate compound can be carried out, for example, by adding the candidate compound to a medium for culturing PINK1-expressing cells or various types of buffers such as a phosphate buffered saline or a Tris-HCl buffer, and then incubating the cells in the mixed solution for a certain period of time. The concentration of the candidate compound to be added may be different depending on the type of the compound, and it can be appropriately selected, for example, from the range of 0.1 nM to 100 nM. The incubation can be preferably carried out for 10 minutes to 24 hours.

Subsequently, the amount of the Ser65-phosphorylated ubiquitin in the cells is measured. The amount of the Ser65-phosphorylated ubiquitin can be measured, for example, by various types of immunological techniques such as ELISA, immunohistochemical staining or immunoblotting, in which the anti-Ser65-phosphorylated ubiquitin antibody is used, or by means such as mass spectrometry, as in the case of detection or quantification of a Ser65-phosphorylated ubiquitin protein in the above described method for testing for Parkinson's disease.

In the screening method of the present embodiment, when the amount of the Ser65-phosphorylated ubiquitin in the cells is significantly increased in comparison to before the contact with the candidate compound, this candidate compound can be evaluated to be promising as a therapeutic agent or a preventive agent for Parkinson's disease. On the other hand, when the Ser65-phosphorylated ubiquitin is detected in the cells only in an amount equivalent to or less than the amount thereof before the contact with the candidate compound, this candidate compound can be evaluated not to be promising as a therapeutic agent or a preventive agent for Parkinson's disease.

Moreover, according to one embodiment, the present invention is a method for screening for a therapeutic agent or a preventive agent for Parkinson's disease, which comprises: (1) a step of preparing a phosphorylation reaction solution containing a ubiquitin protein, a kinase, and a phosphate donor; (2) a step of adding a candidate compound to the phosphorylation reaction solution; and (3) a step of measuring the amount of a ubiquitin protein comprising a phosphorylated serine residue at position 65, which has been generated in the phosphorylation reaction solution. According to the method of the present embodiment, a compound that promotes phosphorylation of Ser 65 of a ubiquitin protein can be obtained as a substance effective for a therapeutic agent or a preventive agent for Parkinson's disease.

The screening method of the present embodiment may be a cell-free system assay, in which a phosphorylation reaction solution containing a ubiquitin protein, a kinase and a phosphate donor is used. The phosphorylation reaction solution of the present embodiment, which is used herein, may be a cell extract prepared from living cells, or an artificial reaction solution prepared by mixing a ubiquitin protein, a kinase and a phosphate donor. The phosphorylation reaction solution of the present embodiment is preferably a cell extract.

When a cell extract is used as such a phosphorylation reaction solution, the cell extract may be prepared from the above described PINK1-expressing cells, or may also be prepared from cells that do not express PINK1.

The "cells that do not express PINK1" of the present embodiment may include not only cells that do not express PINK1 at all, but also cells that do not substantially express PINK1. The cells that do not substantially express PINK1 mean cells, in which the expression of a PINK1 gene cannot be detected by commonly used means for detecting gene expression (e.g., a Northern blotting method, etc.). The cells that do not substantially express PINK1 can be collected, for example, from tissues in an individual animal that do not substantially express PINK1, such as lung, spleen, thymus or leukocytes, according to a method well known to a person skilled in the art. Examples of the individual animal include a mouse, a rat, a rabbit, a dog, non-human primates, and a human. The animal is preferably a human. The cells that do not express PINK1 at all may be collected from a PINK1$^{-/-}$ knockout animal, and the cells may be, for example, the mouse embryonic fibroblasts (MEFs) of a PINK1$^{-/-}$ knockout mouse.

The cell extract of the present embodiment can be prepared by a conventionally known method, such as a method of physically crushing cells or a method of dissolving cells using a surfactant such as CHAPS. The cell extract of the present embodiment is preferably prepared by physically crushing cells.

When the reaction solution prepared by mixing a ubiquitin protein, a kinase and a phosphate donor is used as a phosphorylation reaction solution, such a reaction solution can be prepared by mixing a ubiquitin protein, a kinase and a phosphate donor in a reaction buffer that is suitable for a phosphorylation reaction with kinase. As such a reaction buffer, a Tris-HCl buffer containing $Mg^{2+}$ or $Mn^{2+}$ can be used, for example. The composition of individual components in a phosphorylation reaction solution can be determined, as appropriate, in accordance with the composition of a cell extract prepared from cells.

The ubiquitin protein of the present embodiment may be derived from any given eukaryote. It is preferably derived from mammals such as a mouse, a rat, a rabbit, a dog, non-human primates or a human, and it is particularly preferably human-derived ubiquitin. The ubiquitin protein of the present embodiment can be prepared by biosynthesis involving a genetic engineering method, or chemical synthesis, as in the case of the above-described Ser65-phosphorylated ubiquitin.

As the kinase of the present embodiment, in addition to PINK1, MAP kinase such as ERK1/2, ERK5, ERK7, JNK/SAPK or p38, or any given Ser/Thr kinase such as protein kinase A (PKA), protein kinase C (PKC), CaM kinase, Mos/Raf kinase or cdc2 can be used. The kinase of the present embodiment is preferably PINK1. The kinase of the present embodiment may be derived from any given eukaryote. It is preferably derived from mammals such as a mouse, a rat, a rabbit, a dog, non-human primates or a human, and it is particularly preferably a human-derived kinase. The kinase of the present embodiment can be prepared by biosynthesis involving a genetic engineering method.

As the phosphate donor of the present embodiment, ATP, CTP, GTP, TTP, UTP, dATP, dCTP, dGTP, dTTP, dUTP or the like can be used, for example. The phosphate donor of the present embodiment is preferably ATP or GTP.

Subsequently, a candidate compound is added to the phosphorylation reaction solution. Examples of the candidate compound may be a protein, a peptide, a nucleic acid, a non-peptide compound, a synthetic compound, a cell extract, a plant extract, and an animal tissue extract. These substances may be either novel substances or known substances. The concentration of the candidate compound to be added may be different depending on the type of the compound, and it can be appropriately selected, for example, from the range of 0.1 nM to 100 nM. The phosphorylation reaction can be preferably carried out for 10 minutes to 24 hours.

Subsequently, the amount of the Ser65-phosphorylated ubiquitin in the cells is measured. The amount of the Ser65-phosphorylated ubiquitin can be measured, for example, by various types of immunological techniques such as ELISA, immunohistochemical staining or immunoblotting, in which the anti-Ser65-phosphorylated ubiquitin antibody is used, or by means such as mass spectrometry, as in the case of detection or quantification of a Ser65-phosphorylated ubiquitin protein in the above described method for testing for Parkinson's disease.

In the screening method of the present embodiment, when the amount of the Ser65-phosphorylated ubiquitin in the phosphorylation reaction solution is significantly increased in comparison to before the contact with the candidate compound, this candidate compound can be evaluated to be promising as a therapeutic agent or a preventive agent for Parkinson's disease. On the other hand, when the Ser65-phosphorylated ubiquitin is detected in the phosphorylation reaction solution only in an amount equivalent to or smaller than the amount thereof before the contact with the candidate compound, this candidate compound can be evaluated not to be promising as a therapeutic agent or a preventive agent for Parkinson's disease.

EXAMPLES

Hereinafter, the present invention will be more specifically described in the following examples. However, these examples are not intended to limit the scope of the present invention.

Example 1: Phosphorylation of Ubiquitin Depending on Disappearance of Mitochondrial Membrane Potential 1-1. Phosphorylation of Ubiquitin in CCCP-Treated Cells HeLa cells were cultured in 5% $CO_2$ at 37° C. in Dulbecco's Modified Eagle's Medium (DMEM) (Sigma-Aldrich), to which 1× nonessential amino acid (Lifetec Co., Ltd.), 1× sodium pyruvate (Lifetec Co., Ltd.) and 10% bovine serum (Lifetec Co., Ltd.) had been added. The HeLa cells were treated with 15 to 30 μM CCCP (Wako Pure Chemical Industries, Inc.) for 3 hours, and were then suspended in a cell extraction buffer (20 mM Tris-HCl (pH 7.5), 150 mM NaCl, 1 mM EDTA, and 1% NP-40) to prepare a cell lysate. A cell lysate, which was prepared by the same procedures as those described above with the exception that the CCCP treatment was not performed, was used as a negative control.

The obtained cell lysate was applied to 12.5-15% polyacrylamide gel containing 50 μM Phos-tag acrylamide (Wako Pure Chemical Industries, Inc.) and 100 μM $MnCl_2$, and the obtained mixture was then subjected to electrophoresis. As a control, electrophoresis was carried out using polyacrylamide gel that did not contain Phos-tag. After completion of the electrophoresis, the resulting gel was washed with a transfer buffer containing 0.01% SDS and 1 mM EDTA for 10 minutes, and it was then incubated in a 0.01% SDS transfer buffer that did not contain EDTA for 10 minutes. Thereafter, the resultant was transcribed on a PVDF membrane, and immunoblotting was then carried out thereon, using the anti-ubiquitin antibody P4D1 (Cell Signaling Technology) (1:1000) as a primary antibody, and also using a goat anti-mouse IgG-AP antibody (Santa Cruz Biotechnology, Inc.) (1:10000) as a secondary antibody. Detection was carried out using a BCIP/NBT reagent (Nacalai Tesque).

The results are shown in FIG. 1. The left view of FIG. 1 shows the results obtained by performing electrophoresis using polyacrylamide gel that did not contain Phos-tag, whereas the right view of FIG. 1 shows the results obtained by performing electrophoresis using polyacrylamide gel containing Phos-tag. When the cell lysate subjected to a CCCP treatment was electrophoresed on Phos-tag-containing gel, a band of slow electrophoretic mobility (indicated by an asterisk "*" in the figure) was found. From these results, it was suggested that the ubiquitin would be phosphorylated in the CCCP-treated cells.

1-2. Phosphorylation of Ubiquitin in Cell-Free System

In order to confirm that phosphorylation of ubiquitin takes place due to the disappearance of mitochondrial membrane potential, a ubiquitin phosphorylation assay was carried out in a cell-free system. HeLa cells were subjected to a CCCP treatment by the same procedures as those described in 1-1 above, and the resulting cells were then suspended in a buffer for cell-free assay (20 mM HEPES-KOH (pH 7.5), 220 mM sorbitol, 10 mM KAc, and 70 mM sucrose), to which an EDTA-free protease inhibitor cocktail (Roche Diagnostics) had been added. The cell suspension was passed through a 25-gauge injection needle 30 times to crush the cells, so as to obtain a cell homogenate. Subsequently, the cell homogenate was centrifuged at 4° C. at 800×g for 10 minutes, and after the removal of a nucleus, a supernatant was recovered. The obtained nucleus-free supernatant was further centrifuged at 4° C. at 10,000×g for 20 minutes, so as to recover a mitochondrial pellet.

The mitochondria were incubated at 30° C. for 1 hour in ubiquitin (Boston Biochem), HA-ubiquitin (Boston Biocherm), or $His_6$-ubiquitin (Boston Biochem), each having a final concentration of 40 ng/μL, which had been prepared with a buffer for cell-free system assay, to which 5 mM $MgCl_2$, 5 mM ATP, 2 mM DTT and 1% glycerol had been added. Thereafter, the resultant was centrifuged at 4° C. at 16,000×g for 10 minutes, to remove the mitochondria. The obtained supernatant was subjected to a Phos-tag assay by the same procedures as those described in 1-1 above. A resultant, which was prepared without subjecting to a CCCP treatment, was used as a negative control. The immunoblotting was carried out using an anti-ubiquitin antibody (Dako Japan) (1:500) as a primary antibody, and also using a goat anti-rabbit IgG-AP antibody (Santa Cruz Biotechnology, Inc.) (1:5000) as a secondary antibody. Detection was carried out using a BCIP/NBT reagent (Nacalai Tesque).

Figure 2:
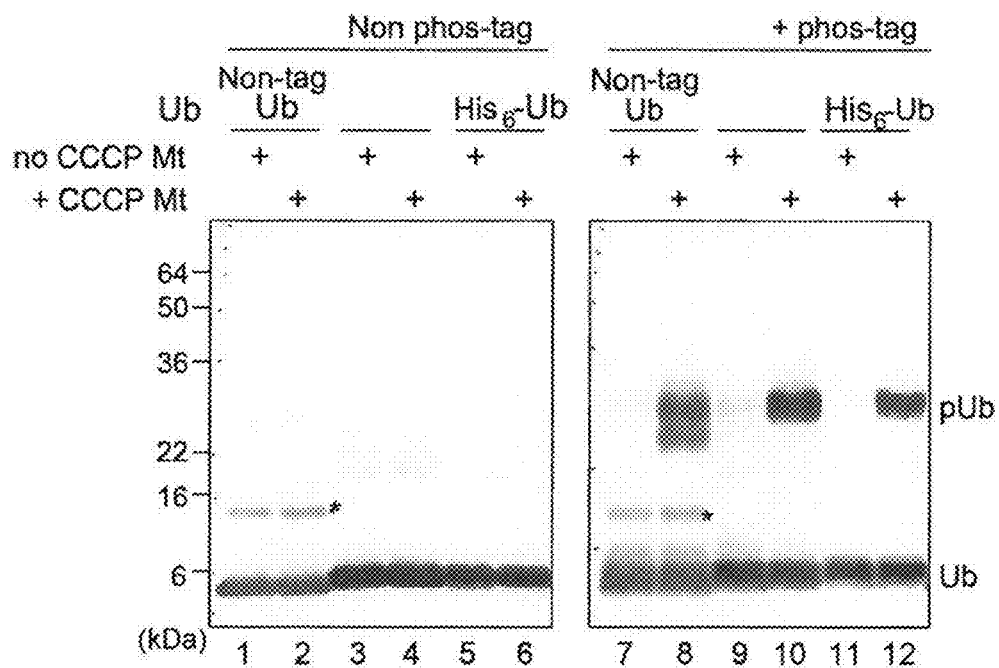
FIG. 2 is a view, in which the phosphorylation of ubiquitin in a cell-free system has been confirmed by a Phos-tag assay.

The results are shown in FIG. 2. The ubiquitin, which was allowed to react with mitochondria isolated from the CCCP-treated cells, was phosphorylated (right view of FIG. 2, lane 8, the band indicated as "pUb"). In contrast, the ubiquitin, which was allowed to react with mitochondria isolated from the cells that had not been subjected to the CCCP treatment, was not phosphorylated (right view of FIG. 2, lane 7). It is to be noted that the band indicated by the asterisk "*" in FIG. 2 is caused by the cross reaction of antibody. From these results, it was demonstrated that phosphorylation of ubiquitin takes place depending on the disappearance of mitochondrial membrane potential. In addition, it was confirmed that even if an HA tag or $His_6$ tag is added to the N-terminus of ubiquitin, phosphorylation of the ubiquitin is not inhibited (right view of FIG. 2, lanes 10 and 12).

Example 2: Phosphorylation Site of Ubiquitin, which is the Serine Residue at Position 65

2-1. Analysis of Phosphorylation Site of Ubiquitin by Mass Spectrometry

In order to specify the phosphorylation site of ubiquitin, an analysis was carried out by liquid chromatography-tandem mass spectrometry (LC-MS/MS). Ubiquitin was allowed to react with CCCP-treated mitochondria in a cell-free system in the same manner as that described in 1-2 above, and it was then subjected to SDS-PAGE. After completion of the electrophoresis, the gel was stained with CCB to detect a band. The gel was washed with ultrapure water, and a band of interest was then excised. The excised gel section was chopped into small sections with a size of 1 $mm^2$, and the sections were then stirred in 1 mL of 50 mM ammonium bicarbonate/50% acetonitrile (ACN) for 1 hour, followed by dehydration. Thereafter, small gel sections were completely dehydrated with 100% ACN. Sequencing Grade Modified Trypsin (Promega), which had been prepared to a concentration of 20 ng/L with 50 mM ammonium bicarbonate/5% ACN (pH 8.0), was added to the small gel sections, and the obtained mixture was then incubated at 37° C. overnight, so as to carry out in-gel trypsin digestion.

After completion of the digestion reaction, 50 μL of 50% ACN/0.1% trifluoroacetic acid (TFA) was added to the reaction product, and the mixture was then shaken for 1 hour to extract a fragmented peptide. The extract was recovered in another tube, and 50 μL of 70% ACN/0.1% TFA was further added to the remaining small gel sections. The obtained mixture was shaken for 30 minutes, so as to carry out additional extraction. The recovered extract was concentrated to 20 μL, using SpeedVac (EYELA). 20 μL of 0.1% TFA was added to the concentrated fragmented peptide to prepare a sample for LC-MS/MS. For the LC-MS/MS, as nanoflow U HPLC apparatuses, Easy-nLC1000 (Thermo Fisher Scientific) and Q-Exactive mass spectrometer (Thermo Fisher Scientific) were used, and as analysis software, Xcalibur (Thermo Fisher Scientific) was used. The spectrum of the fragmented peptide was searched using MASCOT search engine against UniProt database.

Figure 3:
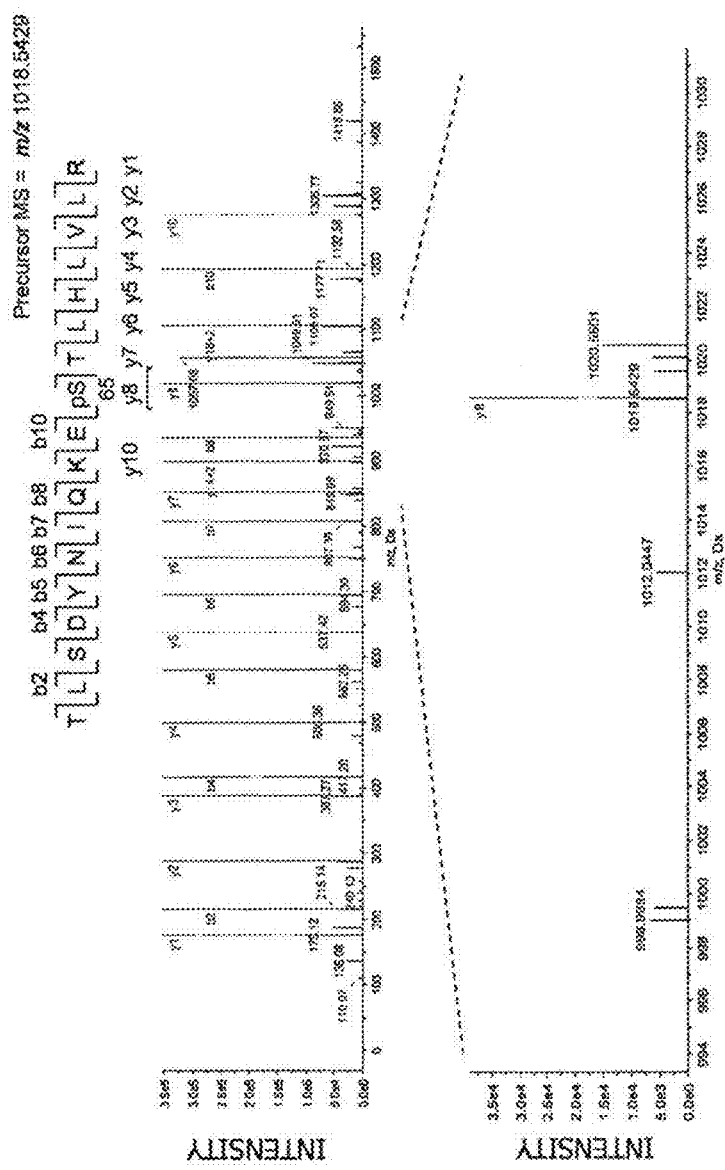
FIG. 3 is a view showing the results of a mass spectrometry performed to specify the phosphorylation site of ubiquitin.

The results are shown in FIG. 3. The ubiquitin-derived peptide fragment, which had been allowed to react with the mitochondria isolated from the CCCP-treated cells, was analyzed. As a result, it was confirmed that the serine at position 65 in a peptide fragment corresponding to the amino acids at positions 55 to 72 of ubiquitin was phosphorylated (TLSDYNIQKE(pS)TLHLVLR). Further, it was also confirmed that the serine at position 65 in a peptide fragment corresponding to the amino acids at positions 64 to 72 of ubiquitin was phosphorylated (E(pS)TLHLVLR). The above described phosphorylated peptide fragment was not detected in the control, which had been allowed to react with the mitochondria isolated from cells not subjected to a CCCP treatment. From these results, it was demonstrated that the serine residue at position 65 (Ser 65) of ubiquitin is a phosphorylation site.

2-2. Analysis of Phosphorylation Site of Ubiquitin in Cell-Free System

In order to further confirm that the Ser 65 of ubiquitin is phosphorylated depending on the disappearance of mitochondrial membrane potential, a recombinant ubiquitin, into the Ser 65 of which a mutation had been introduced, was subjected to a Phos-tag assay by the same procedures as those described in 1-2 above. As such recombinant ubiquitin mutants, a ubiquitin mutant in which the Ser 65 had been substituted with alanine (S65A) and a ubiquitin mutant in which the Ser 65 had been substituted with aspartic acid (S65D) were used, and as a control, wild-type ubiquitin (WT) was used.

The recombinant ubiquitin mutants and the wild-type ubiquitin were prepared by the following procedures. Using a pT7 vector (Sigma-Aldrich), into which DNA encoding the aforementioned mutant or wild-type ubiquitin, to the N-terminus of which a $His_6$ tag sequence had been added, had been incorporated, the *Escherichia coli* Rosetta 2 (DE3) (Novagen) was transformed. The obtained transformant was pre-cultured at 37° C. overnight in 20 mL of LB medium containing 100 μg/mL ampicillin and 24 μg/mL chloramphenicol, and thereafter, the pre-culture was transferred into 200 mL of medium. After completion of the incubation at 37° C. for 2 hours, IPTG (final concentration: 1 mM) was added to the resultant, and the obtained mixture was further cultured for 6 hours. Thereafter, the recovered cells were suspended in 40 mL of 20 mM Tris-HCl (pH 7.5), and was then crushed by an ultrasonic treatment. The resultant was centrifuged at 8,000 rpm for 10 minutes. Thereafter, a supernatant was recovered, was then purified by an ordinary method, and was then dialyzed against buffer A (50 mM Tris-HCl (pH 7.5)/100 mM NaCl/10% glycerol).

Figure 4:
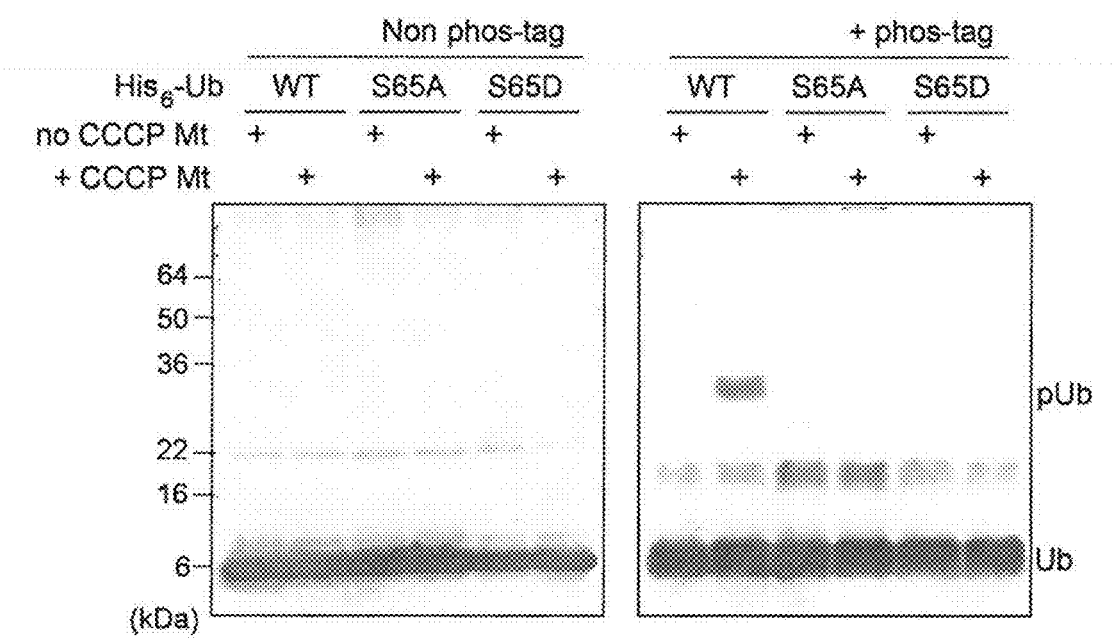
FIG. 4 is a view in which it has been confirmed by a Phos-tag assay that the phosphorylation site of a recombinant ubiquitin in a cell-free system is the serine residue at position 65.

The results are shown in FIG. 4. It was found that the wild-type ubiquitin having Ser 65 was phosphorylated (right view of FIG. 4, lane 2), but that the recombinant ubiquitin mutants having the substituted Ser 65 were both not phosphorylated (right view of FIG. 4, lanes 4 and 6). From these results, it was confirmed that the Ser 65 of ubiquitin is a phosphorylation site.

2-3. Analysis of Phosphorylation Site of Ubiquitin in CCCP-Treated Cells

An extract from CCCP-treated HeLa cells was subjected to a Phos-tag assay by the same procedures as those described in 1-1 above. S65A recombinant ubiquitin and WT ubiquitin were each allowed to express in the HeLa cells by introducing into the cells, a pcDNA3 vector (Invitrogen), into which DNA encoding the recombinant ubiquitin or the WT ubiquitin had been inserted, using FuGENE6 (Roche Diagnostics).

Figure 5:
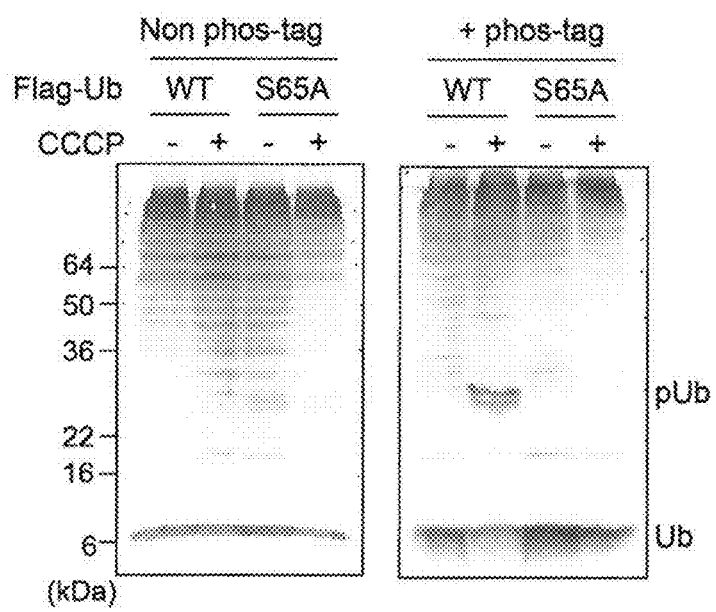
FIG. 5 is a view in which it has been confirmed by a Phos-tag assay that the phosphorylation site of a recombinant ubiquitin in CCCP-treated cells is the serine residue at position 65.

The results are shown in FIG. 5. The wild-type ubiquitin was phosphorylated in the cells (right view of FIG. 5, lane 2), whereas the S65A ubiquitin was not phosphorylated therein (right view of FIG. 5, lane 4). Also from these results, it was confirmed that the Ser 65 of ubiquitin is a phosphorylation site.

Example 3: Phosphorylation of Ubiquitin by PINK1

3-1. Phosphorylation of Ubiquitin in PINK1$^{-/-}$ Cells

It is known that PINK1 is a kinase and is activated depending on the disappearance of mitochondrial membrane potential. Thus, the enzyme that phosphorylates ubiquitin is likely to be PINK1. In order to verify this hypothesis, using the mouse fetal fibroblasts (MEFs) of a PINK1$^{-/-}$ knockout mouse, a phosphorylation test was carried out in a cell-free system.

PINK1$^{-/-}$ MEFs were prepared from PINK1$^{-/-}$ mouse fetuses, and the cells were provided by Jie Shen, Ph. D. (Harvard University). A gene encoding Wild-type PINK1, kinase activity-deleted (KD) mutant PINK1, A168P mutant PINK1 or G386A mutant PINK1 was packaged into a retrovirus, using a pMX-puro vector (COSMO BIO CO., LTD.). By infecting the PINK1$^{-/-}$ MEFs with the obtained retrovirus, wild-type PINK-expressing cells or mutant PINK1-expressing cells were produced. Thereafter, except for the aforementioned operations, a Phos-tag assay was carried out by the same procedures as those described in 1-2 above.

Figure 6:
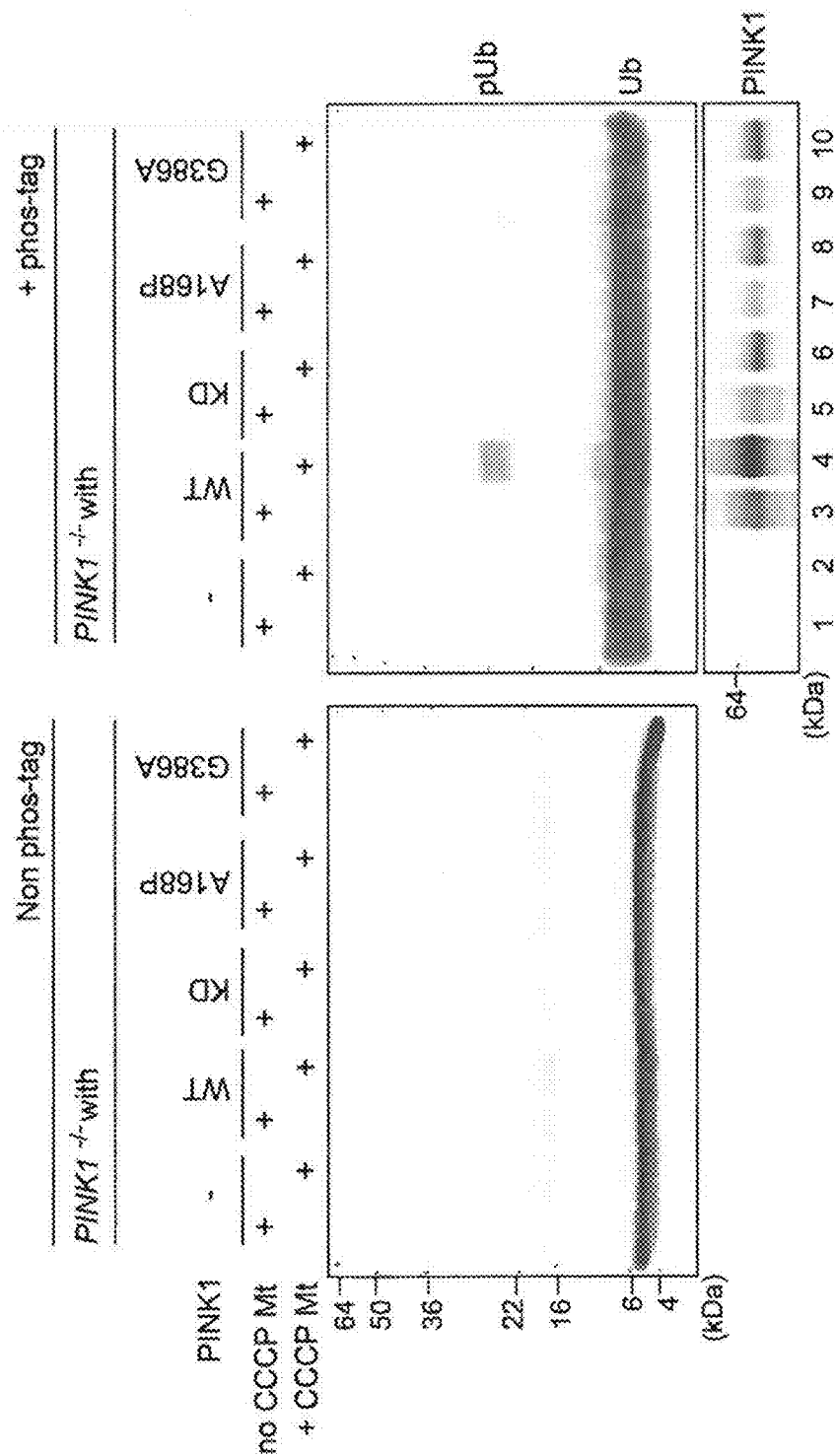
FIG. 6 is a view in which it has been confirmed by a Phos-tag assay that the phosphorylation of ubiquitin is disappeared in PINK1−/− cells.

The results are shown in FIG. 6. It was found that the mitochondria isolated from the CCCP-treated PINK1$^{-/-}$ MEFs did not induce phosphorylation of the ubiquitin (right view of FIG. 6, lane 2), but that the mitochondria isolated from PINK1$^{-/-}$ MEFs, into which wild-type PINK1 had been introduced, induced phosphorylation of the ubiquitin in a CCCP treatment-dependent manner (right view of FIG. 6, lane 4). On the other hand, none of the mitochondria isolated from PINK1$^{-/-}$ MEFs, into which mutant PINK1 having no kinase activity had been introduced, phosphorylated the ubiquitin (right view of FIG. 6, lanes 6, 8 and 10). From these results, it was demonstrated that phosphorylation of ubiquitin is caused by PINK1.

3-2. Phosphorylation of Ubiquitin by PINK1 Isolated from CCCP-Treated Cells

In order to further confirm that PINK1 phosphorylates ubiquitin, PINK1 was isolated from CCCP-treated cells, and whether or not the PINK1 phosphorylates ubiquitin was then examined. Using a pMX-puro vector (COSMO BIO CO., LTD.), a PINK1-3×Flag gene was introduced into HeLa cells, in which the mouse retrovirus receptor mCAT1 had been transiently expressed, by the same procedures as those described in 3-1 above, so as to obtain stable expression cells. The cells were suspended in a buffer for cell-free assay by the same procedures as those described in 1-2 above. Subsequently, the suspension was treated with 10 mg/mL digitonin at 4° C. for 15 minutes, so that the cells were solubilized. Thereafter, the cells were allowed to react with Protein 0 Sepharose 4 Fast Flow (GE Healthcare Life Sciences) conjugated to the anti-FLAG antibody 2H8 (Trans Genic Inc., Ltd.), at 4° C. for 1 hour, so as to carry out immunoprecipitation. The immunoprecipitate obtained after completion of the reaction was washed with the above described buffer, and was then recovered by centrifugation. The obtained immunoprecipitate was electrophoresed by SDS-PAGE, and then, immunoblotting was carried out in the same manner as that described in 1-1 above. For detection of a mitochondrial protein, the anti-VDAC antibody ab2 (Calbiochem) (1:1,000), the anti-mitofusin 2 antibody ab56889 (Abeam) (1:500), and anti-FoF1-ATPase (provided from Ph. D. Ueno) (1:1,000) were used.

Figure 7:
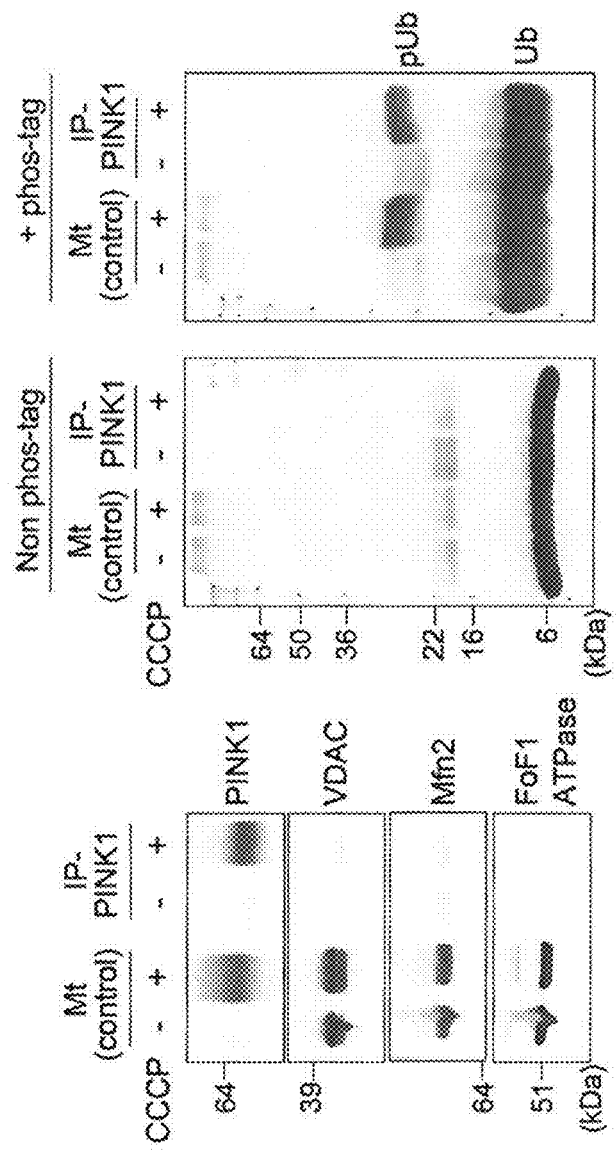
FIG. 7 is a view in which the phosphorylation of ubiquitin by isolated PINK1 has been confirmed by a Phos-tag assay.

The results are shown in FIG. 7. It was demonstrated that, as a result of the immunoprecipitation reaction, only the PINK1 was isolated, and other mitochondrial proteins (VDAC, mitofusin 2, and FoF1-ATPase) were eliminated (left view of FIG. 7).

Subsequently, a Phos-tag assay was carried out by the same procedures as those described in 1-2 above, with the exception, that isolated PINK1 was used instead of mitochondria. In addition, the case of using mitochondria isolated from CCCP-treated cells was used as a control.

The results are shown in FIG. 7. It was demonstrated that PINK1 isolated from CCCP-treated cells phosphorylates ubiquitin, as with mitochondria isolated from CCCP-treated cells (right view of FIG. 7, lane 4). From these results, it was clearly demonstrated that PINK1 phosphorylates the ubiquitin.

Example 4: Ser65-Phosphorylated Ubiquitin, which is Activator for Parkin 4-1. Activation of Parkin by Phosphorylation-Mimicking Form of Ubiquitin in Cells (1)

It is known that if PINK1 is activated, activation of Parkin as an E3 enzyme and the recruitment thereof to mitochondria take place. Hence, in order to examine the role of ubiquitin phosphorylated as a result of activation of PINK1, whether or not Parkin can be activated using a phosphorylation-mimicking form of ubiquitin was examined.

The S65D ubiquitin was used as a phosphorylation-mimicking form of ubiquitin. The S65D ubiquitin was allowed to express in HeLa cells by introducing a pcDNA3 vector (Invitrogen) comprising DNA encoding the S65D ubiquitin into the HeLa cells, using FuGENE6 (Roche Diagnostics). GFP-wild-type Parkin (GFP-Parkin WT) or GFP-mutant Parkin was also expressed in HeLa cells by introducing the vector therein in the same manner as described above. As such GFP-mutant Parkin, Parkin that mimics the phosphorylation of Ser 65, which is essential for activation of the Parkin as an E3 enzyme and the recruitment thereof to mitochondria (GFP-Parkin S65E), and Parkin known as partially activated Parkin, in which the cysteine residue at position 403 is substituted with alanine (GFP-Parkin W403A), were used.

Activation of Parkin as an E3 enzyme was evaluated based on the self-ubiquitination of Parkin. An intracellular ubiquitination assay was carried out by isolating a cytoplasmic fraction of HeLa cells, containing GFP-Parkin or GFP-mutant Parkin and a wild-type ubiquitin or a phosphorylation-mimicking form of ubiquitin, from the cells by the same procedures as those described in 1-1 above, and then subjecting the isolated fraction to immunoblotting. A CCCP treatment was carried out by the same procedures as those described in 1-1 above.

Figure 8:
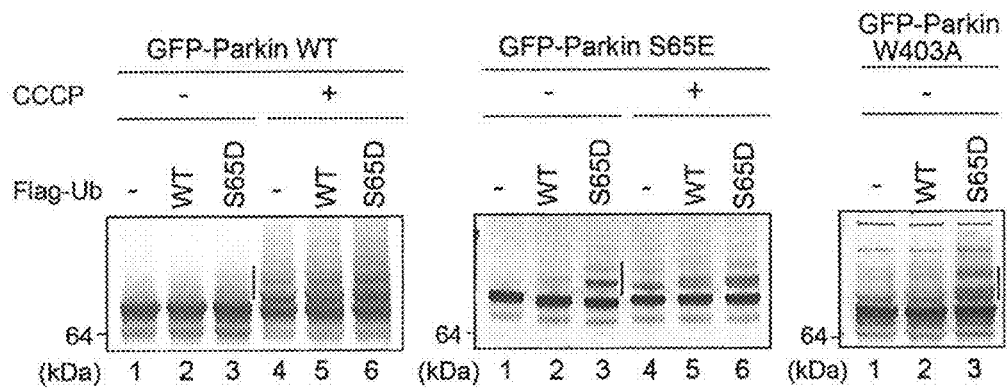
FIG. 8 is a view in which the activation of Parkin by a phosphorylation-mimicking form of ubiquitin has been confirmed by an intracellular ubiquitination assay.

The results are shown in FIG. 8. The S65D recombinant ubiquitin did not activate wild-type Parkin in the absence of a CCCP treatment, that is, under conditions in which PINK1 was not activated (left view of FIG. 8, lane 3). On the other hand, it was demonstrated that the S65E recombinant Parkin and the W403A recombinant Parkin were activated by the S65D recombinant ubiquitin even in the absence of a CCCP treatment (central view of FIG. 8, lane 3, and right view of FIG. 8, lane 3). From these results, it was suggested that a phosphorylated ubiquitin could be an activator for Parkin.

4-2. Activation of Parkin by Phosphorylation-Mimicking Form of Ubiquitin in Cells (2)

In order to further examine the role of a phosphorylated ubiquitin in activation of Parkin, an intracellular ubiquitination assay was carried out by the same procedures as those described in 4-1 above, using mutant ubiquitin (GGAA or GGVV) and a recombinant phosphorylation-mimicking form of ubiquitin (S65DGGAA or S65DGGVV), with a deletion of a glycine residue at the C-terminus of ubiquitin, which is necessary for the formation of a polyubiquitin chain.

Figure 9:
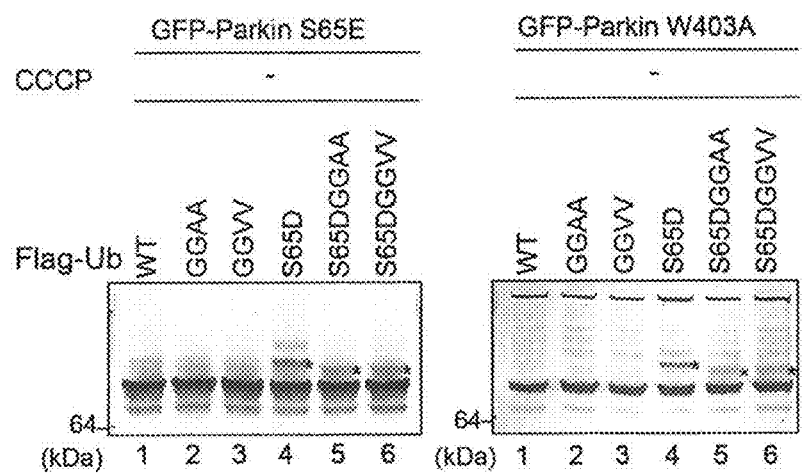
FIG. 9 is a view in which Parkin activation by a C-terminus-modified ubiquitin protein has been confirmed by an intracellular ubiquitination assay.

The results are shown in FIG. 9. It was demonstrated that the S65D phosphorylation-mimicking form of ubiquitin with a deletion of the glycine residue at the C-terminus thereof also activates the S65E recombinant Parkin and the W403A recombinant Parkin, as with the S65D phosphorylation-mimicking form of ubiquitin having the glycine residue at the C-terminus thereof (FIG. 9, lanes 4 to 6). From these results, it was suggested that the phosphorylated ubiquitin could not be used for a polyubiquitin chain added by Parkin, but that it functions as an activator for Parkin based on a mechanism independent from the polyubiquitin chain.

Example 5: Ubiquitin Added to Substrate Protein on Mitochondria, which May not be Phosphorylated 5-1. Visualization Analysis of Ubiquitination of Mitochondria by Multiple Fluorescence Immunostaining In order to further verify the matter suggested in 4-2 above, whether or not unphosphorylated S65A mutant ubiquitin is added to a substrate protein on mitochondria was examined. The S65A mutant ubiquitin was allowed to express in HeLa cells by the same procedures as those described in 2-3 above. In addition, wild-type ubiquitin allowed to express in HeLa cells was used as a control. A CCCP treatment was carried out by the same procedures as those described in 1-1 above.

The cells were fixed using 4% formaldehyde, and were then solubilized with 50 mg/mL digitonin. Thereafter, immunostaining was carried out using the anti-GFP antibody ab6556 (Abcam) (1:500), the anti-Flag antibody 2H8 (Trans Genie Inc., Ltd.) (1:500) and the anti-Tom20 antibody FL-145 (Santa Cruz Biotechnology, Inc.) (1:3,000) as primary antibodies, and also using Alexa Fluor 488 or 568-labeled anti-mouse or rabbit IgG antibody (Invitrogen) (1:2,000) as a secondary antibody. After completion of the staining, the cells were observed using a confocal laser scanning microscope system LSM510 (Carl Zeiss). In the statistical analysis, 100 or more cells were analyzed through three experiments, and a Student's t-test was carried out.

Figure 10:
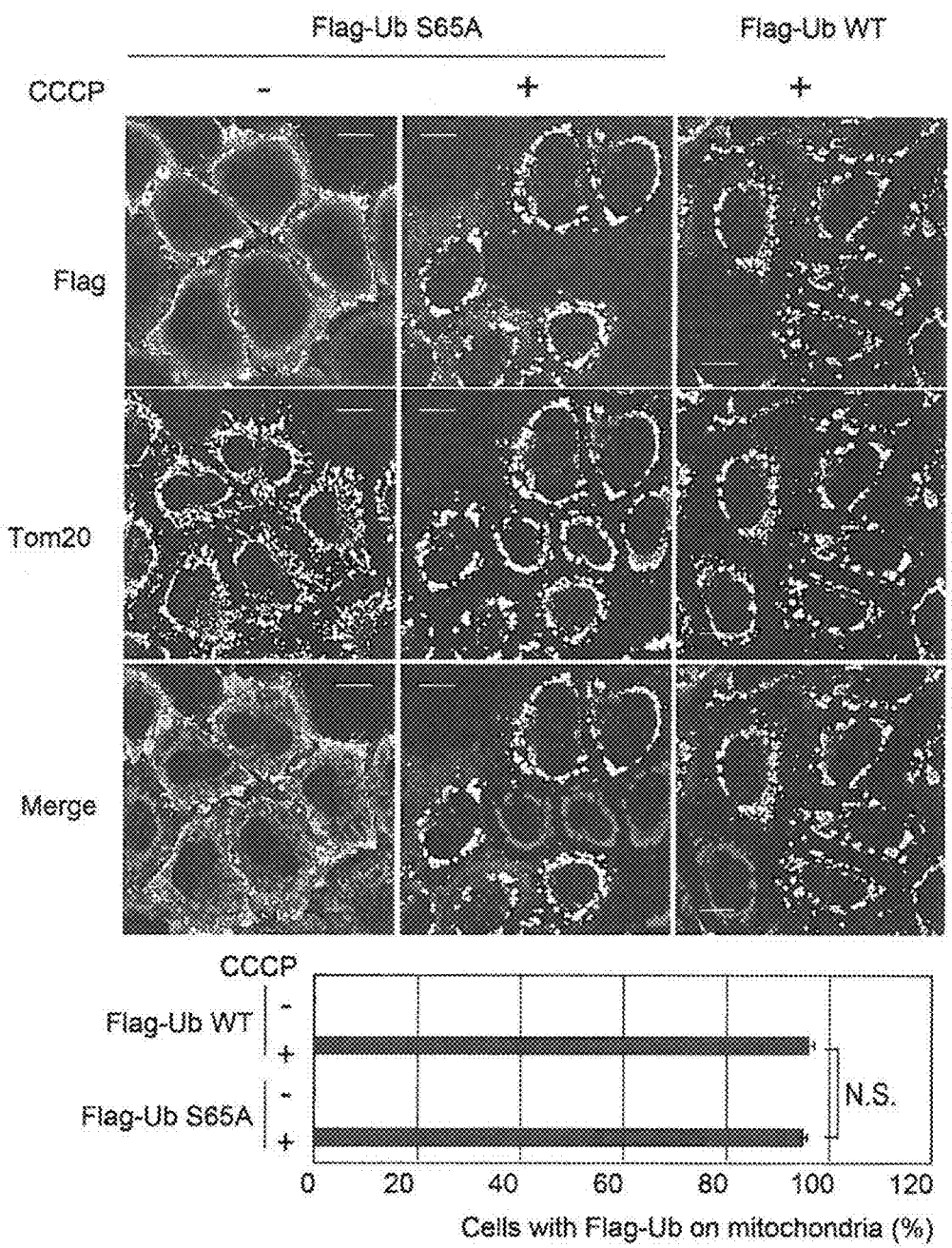
FIG. 10 includes multiple fluorescence immunostained images showing the ubiquitination of mitochondria.

The results are shown in FIG. 10. It was demonstrated that the unphosphorylated S65A recombinant ubiquitin is also added to a substrate protein on mitochondria, as with the wild-type ubiquitin. From these results as well, it was confirmed that the polyubiquitin chain added by Parkin is not limited to one derived from phosphorylated ubiquitin.

Example 6: Ser65-Phosphorylated Ubiquitin Essential for Complete Activation of Parkin 6-1. Activation of Parkin by Ser65-Phosphorylated Ubiquitin in Cell-Free System Finally, activation of Parkin was evaluated by a cell-free system, in which recombinant Parkin and recombinant ubiquitin or Ser65-phosphorylated ubiquitin were used. WT, S65E or W403A GFP-Parkin was prepared from HeLa cells or PINK1⁻ MEFs, which had not been treated with CCCP, by the following procedures. The cells were suspended in a buffer for cell-free assay (20 mM HEPES-KOH (pH 7.5), 220 mM sorbitol, 10 mM KAc, and 70 mM sucrose), to which an EDTA-free protease inhibitor cocktail (Roche Diagnostics) had been added. The cell suspension was passed through a 25-gauge injection needle 30 times to crush the cells, so as to obtain a cell homogenate. Subsequently, the cell homogenate was centrifuged at 4° C. at 800×g for 10 minutes, and after the removal of nuclei, a supernatant was recovered. The thus obtained nucleus-free supernatant was further centrifuged at 4° C. at 16,000×g for 20 minutes to recover a supernatant, thereby obtaining a cytoplasmic fraction from which the mitochondria were removed. To this supernatant, 5 mM $MgCl_2$, 5 mM ATP, 2 mM DTT and 1% glycerol were added. WT, S65A or S65D $His_6$-ubiquitin, or $His_6$-Ser65-phosphorylated ubiquitin, was prepared by the same procedures as those described in 2-1 and 2-2 above.

Activation of Parkin as an E3 enzyme was evaluated based on the self-ubiquitination of the Parkin. A cell-free ubiquitination assay was carried out by adding the wild-type ubiquitin, S65D recombinant ubiquitin or Ser65-phosphorylated ubiquitin (final concentration 50 µg/mL), prepared by the procedures described in 1-2 and 2-1 above, to a cytoplasmic fraction of HeLa cells containing GFP-Parkin or GFP-recombinant Parkin, and then incubating the obtained mixture at 30° C. for 2 hours.

Figure 11:
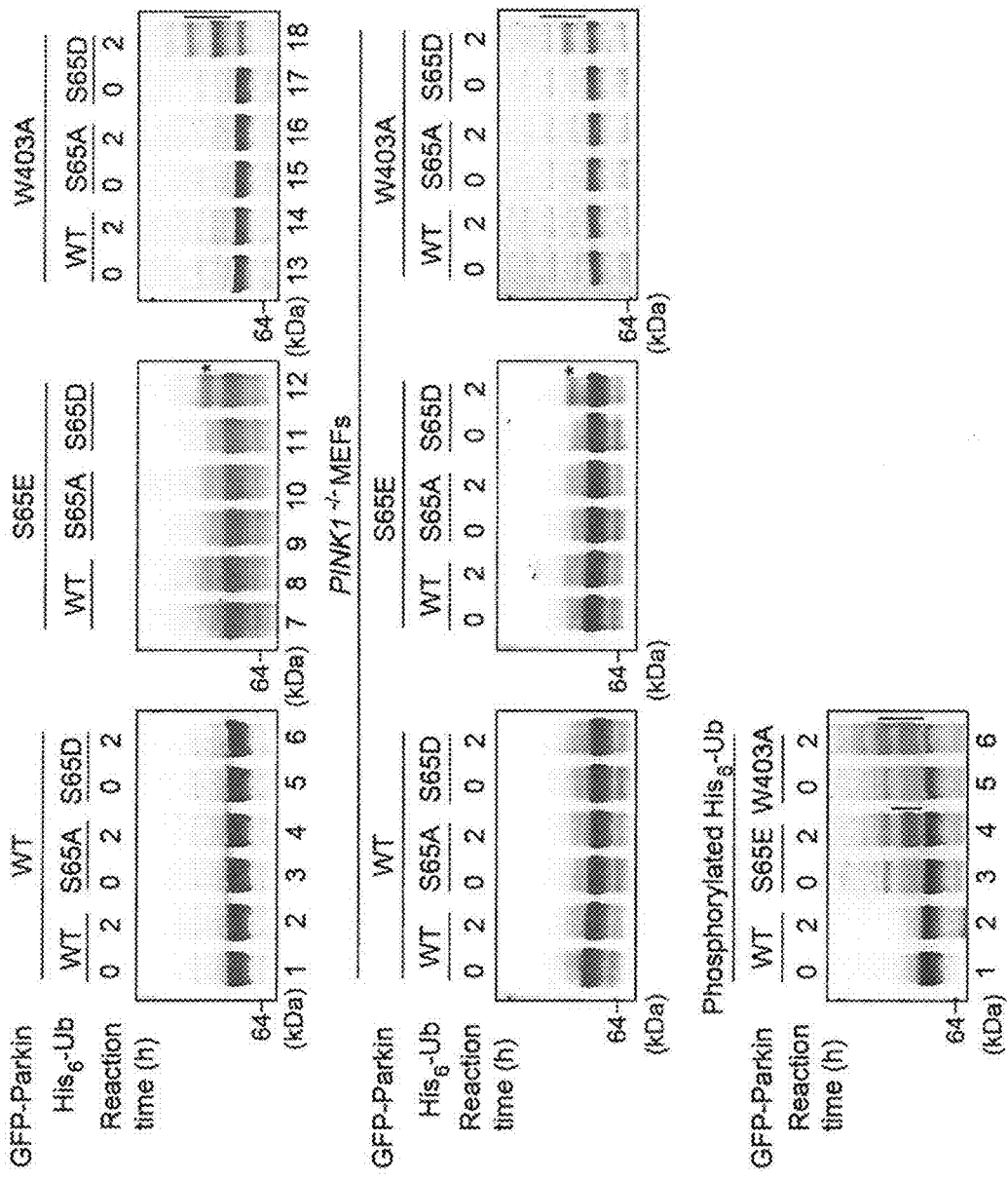
FIG. 11 is a view showing the activation of Parkin by a recombinant ubiquitin or ubiquitin comprising a phosphorylated serine residue at position 65 in a cell-free system.

The results are shown in FIG. 11. The S65E recombinant Parkin and the W403A recombinant Parkin were activated by an S65D phosphorylation-mimicking form of ubiquitin, even though mitochondria having no membrane potential were missing (upper case of FIG. 11, lanes 12 and 18), but the wild-type Parkin was not activated by the S65D phosphorylation-mimicking form of ubiquitin (upper case of FIG. 11, lane 6). The wild-type ubiquitin or the S65A recombinant ubiquitin did not activate the S65E recombinant Parkin and the W403A recombinant Parkin (upper case of FIG. 11, lanes 10 and 16). Moreover, although the influence of PINK1 was eliminated, exactly the same results were obtained (middle case of FIG. 11). Furthermore, it was confirmed that the same results as described above were obtained even in the case of using ubiquitin, the Set 65 of which was actually phosphorylated, instead of the S65D phosphorylation-mimicking form of ubiquitin (lower case of FIG. 11).

Figure 12:
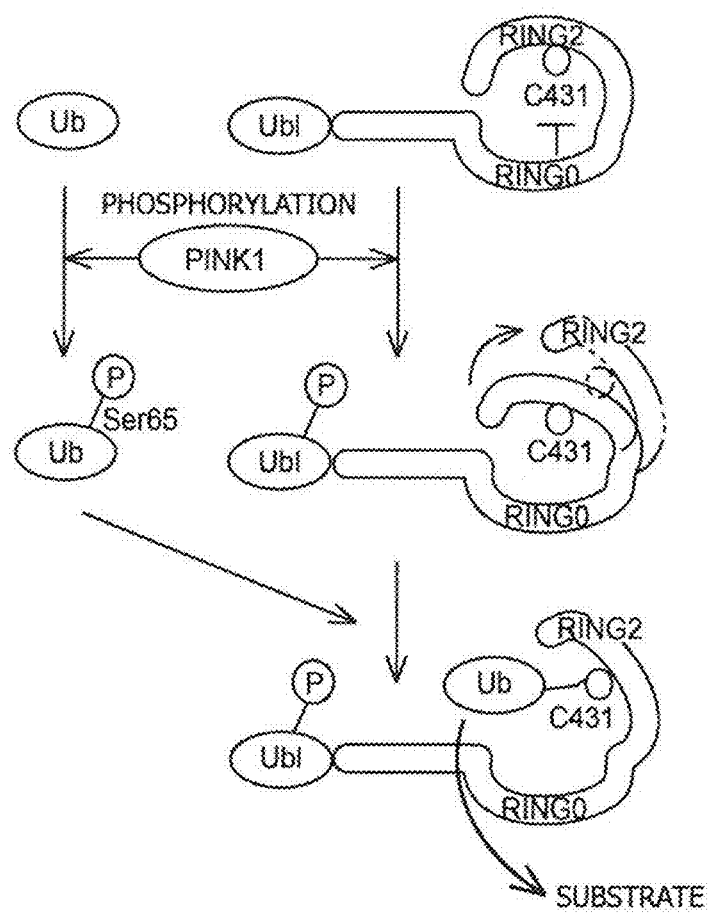
FIG. 12 is a schematic view showing the mechanism of activation of Parkin.

The mechanism of activation of Parkin assumed from the aforementioned results of the Examples is shown in FIG. 12. The activated PINK1 phosphorylates both Parkin and ubiquitin. In addition, phosphorylation of Parkin by PINK1 is necessary for activation of the Parkin. However, only partial activation of Parkin takes place by phosphorylation of the Parkin by PINK1, and for complete activation of the Parkin, the presence of ubiquitin, the Ser 65 of which is phosphorylated, is necessary.

Thus, it was confirmed that the Ser65-phosphorylated ubiquitin according to the present invention is a constitutional molecule essential for activation of Parkin, and that the present Ser65-phosphorylated ubiquitin can be used as a biomarker for detecting Parkinson's disease. Moreover, it was suggested that, using the biomarker for detecting Parkinson's disease according to the present invention, a method for screening for a therapeutic agent or a preventive agent for Parkinson's disease can be provided. Furthermore, it was also suggested that the Ser65-phosphorylated ubiquitin and the Ser65Asp phosphorylation-mimicking ubiquitin have the effect of activating Parkin, and can be used as therapeutic agents or preventive agents for Parkinson's disease.

Example 7: Production of Anti-Ser65-Phosphorylated Ubiquitin Antibody

Subsequently, an antibody having an ability to specifically bind to the Ser65-phosphorylated ubiquitin was produced. A rabbit was immunized with CNIQKE(pS)TLH, which is a ubiquitin fragment comprising phosphorylated Ser 65, and a guinea pig was immunized with CNIQKE(pS)TLHLV, 4 or 5 times at intervals of 2 weeks. Thereafter, whole blood was collected from each animal, and serum was then obtained, thereby obtaining antiserum containing a polyclonal antibody.

The binding ability of the obtained polyclonal antibody was evaluated using a ubiquitin sample prepared by the same procedures as those described in 1-2 above. In addition, as a positive control, the anti-ubiquitin antibody Z0458 (Dako) was used.

Figure 13:
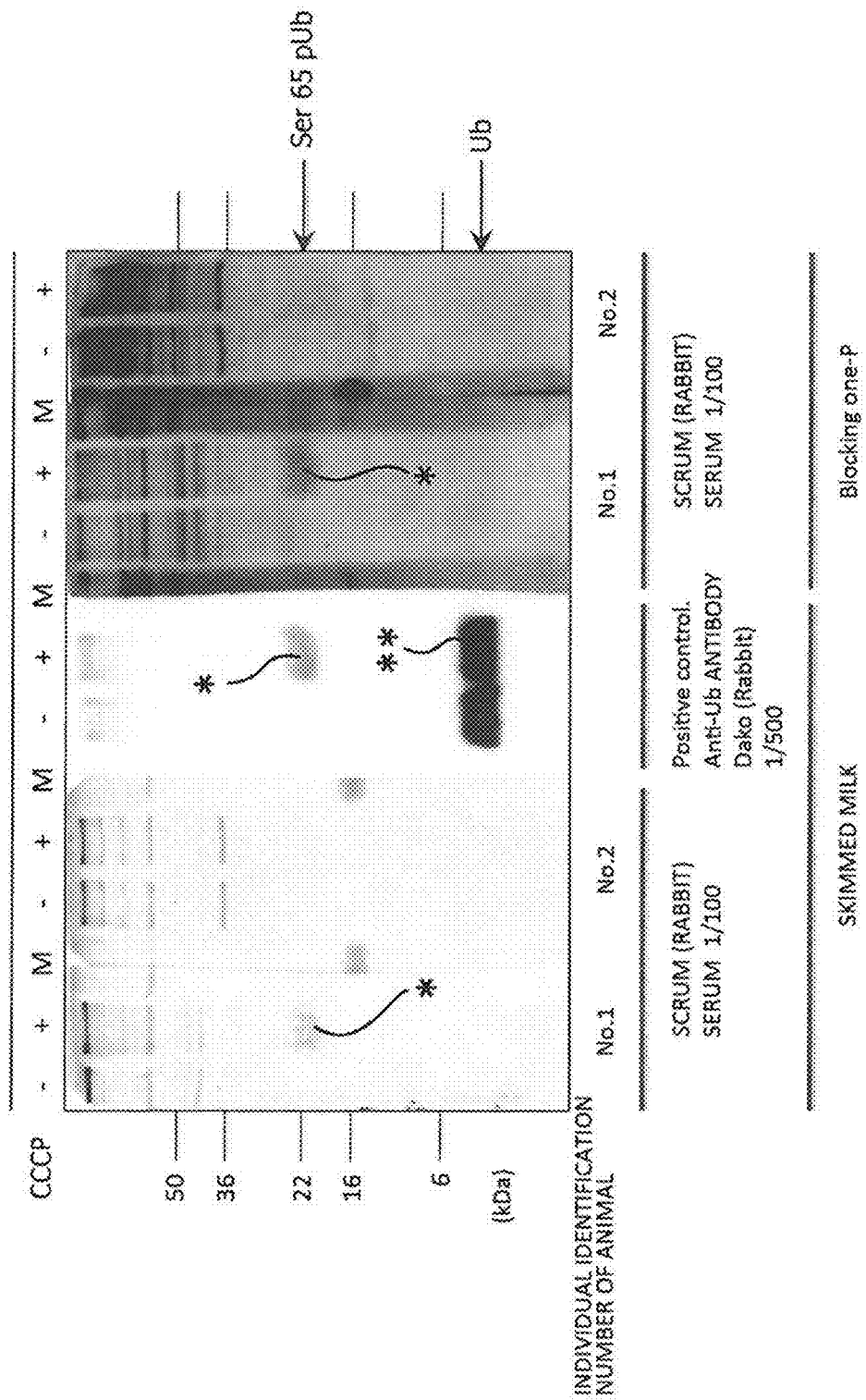
FIG. 13 is a view showing the detection of ubiquitin comprising a phosphorylated serine residue at position 65, using an anti-phosphorylated ubiquitin rabbit polyclonal antibody.
Figure 14:
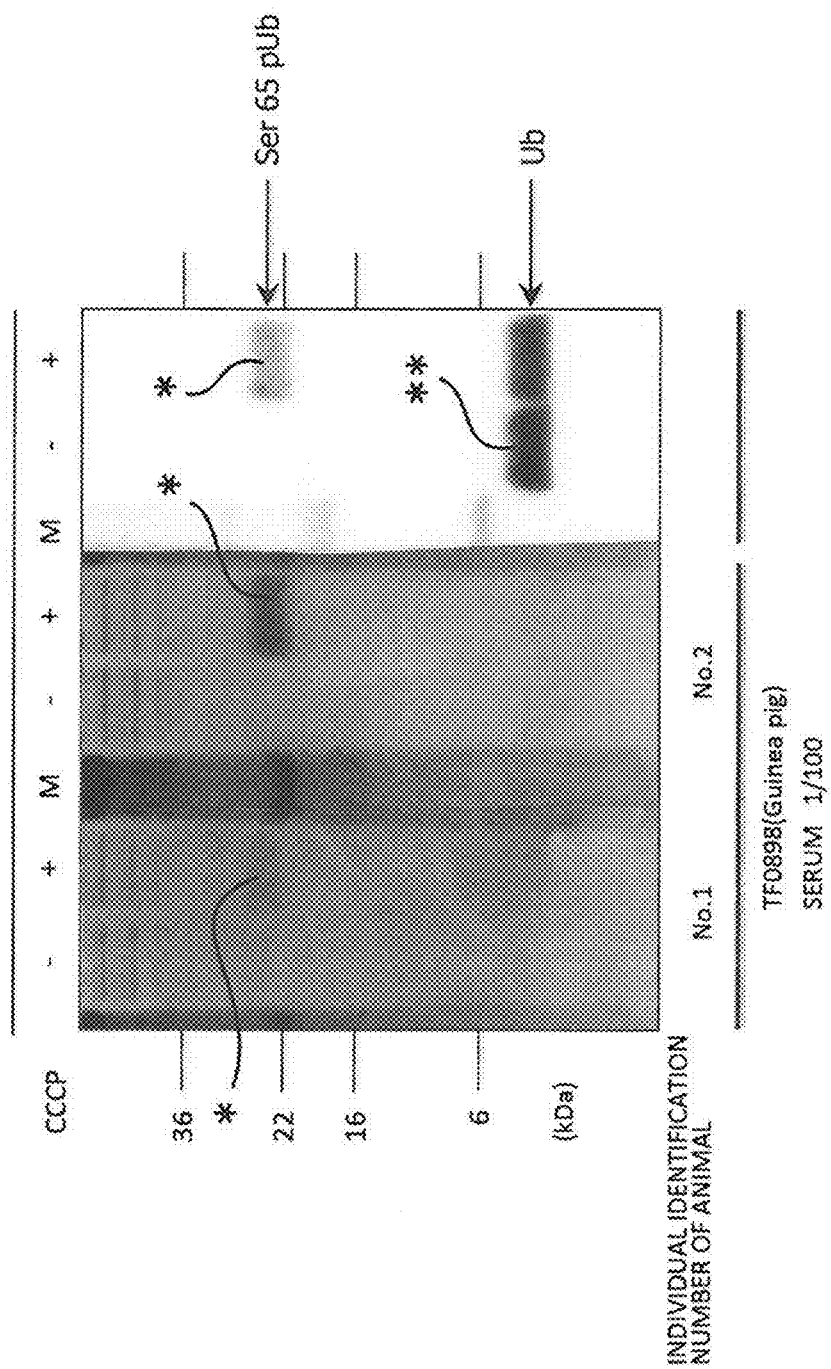
FIG. 14 is a view showing the detection of ubiquitin comprising a phosphorylated serine residue at position 65, using an anti-phosphorylated ubiquitin guinea pig polyclonal antibody.

The results are shown in FIG. 13 and FIG. 14. In the positive control, both phosphorylated ubiquitin (in the figure, indicated by the asterisk "*") and unphosphorylated ubiquitin (in the figure, indicated by the double asterisk "**") were detected. In contrast, both the anti-ubiquitin rabbit polyclonal antibody and the anti-ubiquitin guinea pig polyclonal antibody specifically detected only the phosphorylated ubiquitin.

As such, it was suggested that the anti-Ser65-phosphorylated ubiquitin antibody according to the present invention have an ability to specifically bind to the Ser65-phosphorylated ubiquitin, and that the present anti-Ser65-phosphorylated ubiquitin antibody can be used in the above described method for detecting Parkinson's disease.

Example 8: Detection of Ser65-Phosphorylated Peptide by Mass Spectrometry

In order to confirm whether or not the Ser 65 of ubiquitin is actually phosphorylated in vive depending on the disappearance of mitochondrial membrane potential, an LC-MS/MS measurement was carried out on a cell extract. A cell extract was prepared from CCCP-treated or CCCP-untreated HeLa cells by the same procedures as those described in 1-1 above, and it was then subjected to SDS-PAGE. Subsequently, peripheral gel corresponding to the molecular weight of ubiquitin was excised, and a sample was then prepared in the same manner as that described in 2-1 above. The prepared sample was subjected to a mass spectrometric analysis using an LC-MS/MS apparatus. Upon cleavage with protease, in addition to trypsin (Promega), endoproteinase Lys-C (Wako Pure Chemical Industries, Inc.) was used. After completion of the LC-MS/MS measurement, with regard to fragment ions derived from a phosphorylated peptide (E(pS)TLHLVLR) and a non-phosphorylated peptide (ESTLHLVLR), corresponding to the amino acids at positions 64 to 72 of the ubiquitin, the area under the curves (AUC) was calculated using PinPoint software (Thermo Fisher Scientific).

Figure 15:
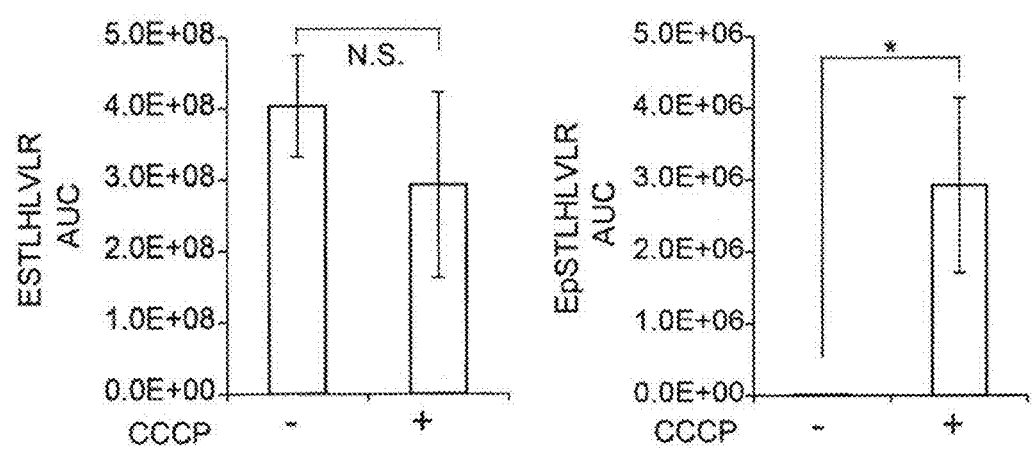
FIG. 15 is a view in which the presence of ubiquitin comprising a phosphorylated serine residue at position 65 in a cell has been confirmed by mass spectrometry.

The results are shown in FIG. 15. A signal derived from the phosphorylated peptide fragment (E(pS)TLHLVLR) was detected in the extract of the CCCP-treated HeLa cells, whereas such a phosphorylated peptide fragment was not detected in the extract of the CCCP-untreated HeLa cells. A signal derived from the non-phosphorylated peptide fragment (ESTLHLVLR) was detected in the cell extracts of both the CCCP-treated and CCCP-untreated HeLa cells. From these results, it was demonstrated that the phosphorylation of the Ser 65 of ubiquitin, which actually takes place in vivo depending on the disappearance of mitochondrial membrane potential, can be detected by mass spectrometry.

The invention claimed is:

1. An antibody having an ability to specifically bind to a ubiquitin protein comprising a phosphorylated serine residue at position 65, wherein the antibody specifically binds to an epitope present within amino acid residues 59 to 69 of SEQ ID NO:1.

2. The antibody according to claim 1, which is a polyclonal antibody or a monoclonal antibody.

* * * * *

UNITED STATES PATENT AND TRADEMARK OFFICE
CERTIFICATE OF CORRECTION

| | | |
|---|---|---|
| PATENT NO. | : 9,804,174 B2 | |
| APPLICATION NO. | : 15/119645 | |
| DATED | : October 31, 2017 | |
| INVENTOR(S) | : Matsuda et al. | |

It is certified that error appears in the above-identified patent and that said Letters Patent is hereby corrected as shown below:

In the Specification

Column 9, Line 9: Please correct "(PASTA," to read -- (FASTA, --

Column 16, Line 64: Please correct "of 20 ng/L" to read -- of 20 ng/µL --

Column 21, Line 60: Please correct "the Set 65 of" to read -- the Ser 65 of --

Signed and Sealed this
Twenty-fourth Day of April, 2018

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 76
<212> TYPE: PRT
<213> ORGANISM: Homo sapiens
<220> FEATURE:
<221> NAME/KEY: MOD_RES
<222> LOCATION: (65)..(65)
<223> OTHER INFORMATION: PHOSPHORYLATION

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 76
<212> TYPE: PRT
<213> ORGANISM: Homo sapiens

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Asp Thr Leu His Leu Val Leu Arg Leu Arg Gly Gly
65                  70                  75
```